United States Patent
Qin et al.

(10) Patent No.: US 11,529,309 B2
(45) Date of Patent: Dec. 20, 2022

(54) COMPOSITIONS, METHODS AND KITS FOR TREATING A CONTACT LENS

(71) Applicant: University of Houston System, Houston, TX (US)

(72) Inventors: Guoting Qin, Pearland, TX (US); Chengzhi Cai, Pearland, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 228 days.

(21) Appl. No.: 16/096,603

(22) PCT Filed: Apr. 28, 2017

(86) PCT No.: PCT/US2017/030065
§ 371 (c)(1),
(2) Date: Oct. 25, 2018

(87) PCT Pub. No.: WO2017/189967
PCT Pub. Date: Nov. 2, 2017

(65) Prior Publication Data
US 2019/0133932 A1      May 9, 2019

Related U.S. Application Data

(60) Provisional application No. 62/329,388, filed on Apr. 29, 2016.

(51) Int. Cl.
| | | |
|---|---|---|
| A61K 31/496 | (2006.01) | |
| A61K 9/00 | (2006.01) | |
| A61L 12/10 | (2006.01) | |
| C07C 271/12 | (2006.01) | |
| C07C 271/14 | (2006.01) | |
| C07D 215/56 | (2006.01) | |

(52) U.S. Cl.
CPC .......... *A61K 9/0051* (2013.01); *A61K 31/496* (2013.01); *A61L 12/10* (2013.01); *C07C 271/12* (2013.01); *C07C 271/14* (2013.01); *C07D 215/56* (2013.01)

(58) Field of Classification Search
None
See application file for complete search history.

(56) References Cited

U.S. PATENT DOCUMENTS 4,559,341 A * 12/1985 Petersen ............. C07D 231/12
                                                  514/253.08
4,559,351 A * 12/1985 Stoss .................... C07D 211/90
                                                  514/338

(Continued)

OTHER PUBLICATIONS

Gattás-Asfura et al., Perfluorinated Alginate for Cellular Encapsulation, J Biomed Mater Res A Aug. 2012;100(8):1963-71, printed from https://pubmed.ncbi.nlm.nih.gov/22544596/?utm_source=gquery &utm_medium=referral&utm_campaign=CitationSensor, 1 page, abstract only.*

(Continued)

*Primary Examiner* — Gigi G Huang
(74) *Attorney, Agent, or Firm* — Jackson Walker LLP

(57) ABSTRACT

Provided herein are fluorinated compounds having chemical structures: (I) where n is 0 or greater, or (II) where m and n are 0 or greater, or an amino acid, a soluble polymer, an oligo(ethylene glycol), a poly(ethylene glycol), or a carbohydrate each fluorinated with perfluorocarbons having the chemical structure (III) where n is 0 or greater. These fluorinated compounds are utilized in contact lenses to impart lipid-resistant, protein-resistant and biofouling-resistant properties, thus reducing discomfort and infection caused by contact lens wear without changing its transmission characteristics. Also provided is an ophthalmic drug delivery system comprising at least one of the compounds described above embedded in the contact lens and a kit to incorporate the ophthalmic into a contact lens. Methods for incorporating these compounds onto a contact lens without affecting transparency and for use in treating an ophthalmologic-associated condition are provided.

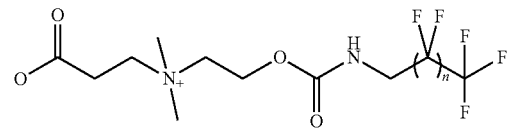

(I)

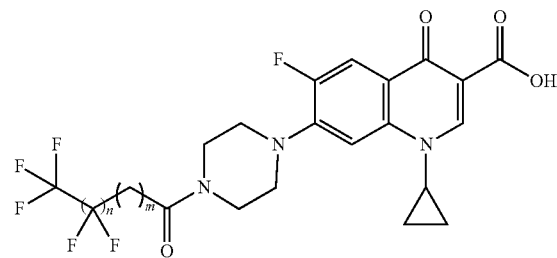

(II)

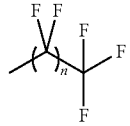

(III)

9 Claims, 9 Drawing Sheets

(56) References Cited

U.S. PATENT DOCUMENTS

| | | | | |
|---|---|---|---|---|
| 6,482,799 | B1* | 11/2002 | Tuse | A61L 12/14 |
| | | | | 422/28 |
| 8,263,040 | B2* | 9/2012 | Platzek | A61K 49/0433 |
| | | | | 424/1.73 |
| 2009/0291073 | A1* | 11/2009 | Ward | C12N 15/1137 |
| | | | | 424/130.1 |
| 2010/0330146 | A1* | 12/2010 | Chauhan | A61P 27/02 |
| | | | | 424/424 |

OTHER PUBLICATIONS

Mitsos, Isosteres in Medicinal Chemistry—H to F replacement, Definition of Bioisosterism, www.scrips.edu, Feb. 1, 2006, printed from https://www.scripps.edu/baran/images/grpmtgpdf/Mitsos_Feb_06.pdf, 7 pages.*

Franklin et al. "Surface elemental analysis of contact lenses using X-ray photoelectron spectroscopy (XPS): What techniques are available and how do the results compare?." Contact Lens and Anterior Eye 41 (2018): S65.*

García-Porta et al, Performance of Three Multipurpose Disinfecting Solutions with a Silicone Hydrogel Contact Lens, BioMed Research International, vol. 2015, Article ID 216932, 13 pages, Mar. 31, 2015.*

* cited by examiner

COMPOSITIONS, METHODS AND KITS FOR TREATING A CONTACT LENS

CROSS-REFERENCE TO RELATED APPLICATION

This application is a national stage application under 35 U.S.C. § 371 of pending international application PCT/US2017/030065, filed Apr. 28, 2017, which claims priority under 35 U.S.C. § 119(e) of provisional application U.S. Ser. No. 62/329,388, filed Apr. 29, 2016, the entirety of both of which are hereby incorporated by reference.

BACKGROUND OF THE INVENTION

Field of the Invention

The present invention relates generally to the field of contact lenses. More specifically, the present invention relates to methods for modifying contact lenses into a drug delivery system. The present invention further relates to contact lenses which are lipid-resistant, protein-resistant and biofouling-resistant, thus reducing discomfort and infection caused by contact lens wear.

Description of the Related Art

Currently more than 90% of ophthalmic drugs are delivered in the form of eye drop solutions. Only ~1-7% of the administered dose, however, is actively absorbed from such eye drop solutions. Therefore, high drug dosage and frequent administration are necessary in order to have a therapeutic effect, which results in undesired toxicity and low patient compliance. Patient compliance is necessary to achieve desired treatment efficacy, management of postoperative ocular pain and inflammation, and prevent chronic diseases such as glaucoma.

In the search for alternative approaches, contact lenses as ocular drug delivery systems have attracted tremendous attention due to high ocular drug availability, less frequent administration, and low drug toxicity, which could potentially provide a more convenient treatment regimen and better patient compliance.

Approaches to incorporate drugs into contact lenses have evolved in recent years, including simple immersion, covalent binding, molecular imprinting, layer-by-layer technique and incorporation with nanoscaled materials. Each method has its own advantages in one or two areas, but unfortunately, none to date have provided a simple manufacture process, high drug loading efficacy, satisfactory drug release kinetics, and high lens quality after drug incorporation despite rapid developments in this field.

Contact lenses have garnered significant popularity in the last few decades. Besides functional or optical reasons, many people choose to wear contact lenses for aesthetic and cosmetic factors. However, discomfort and infection remains two major complications associated with contact lens wear. Of the approximately 140 million contact lens wearers worldwide, 21-50% suffer from contact lens discomfort. This is the major reason why individuals stop wearing contact lenses and is a major challenge to the contact lens industry.

Research has revealed that contact lens discomfort involves a series of complex processes including, but not limited to, lipid deposition, oxidized lipid product deposition, protein deposition, protein denaturation. These processes trigger host responses such as kinin influx and activation, and ocular mucin profile alternations. These processes are most likely caused by the disturbance of the native environment of ocular surface induced by the insertion of lens that is usually about ten times thicker than tear film.

Additionally, the absorption of tear film components onto the contact lens and/or the release of molecules from the contact lens to the tear film disturb the delicate balance of molecules in the tear film, resulting in tear film instability following a series of cellular responses at the ocular surface. Further, contact lenses can serve as an incubator for microorganisms such as bacteria that increases the risk of overt infection. Eye infection, which is often caused by adhesion and colonization of bacteria such as *Pseudomonas aeruginosa* and *Staphylococcus aureus*, on contact lenses can be dangerous for a user's eyesight.

To reduce, or eliminate if possible, contact lens discomfort and contact lens infection, it is highly desirable to maintain the native environment of the ocular surface including the composition of lipids, proteins, and other components in the tear film, as well as their bioactivity, even though the mechanical effects of the contact lens on eyelids and ocular surface are almost inevitable.

Silicone hydrogel lenses, one of the most commonly used types of contact lenses, are generally more hydrophobic, and thus attract more lipids and less proteins compared to other types of hydrogel lenses. However, proteins on silicone hydrogel lenses tend to denature more easily than on other types of contact lenses, making protein an equal contributor as lipid to the discomfort when wearing silicone hydrogel contact lenses.

Extensive efforts have been made to reduce the discomfort and infections associated with contact lens wear by limiting the deposition of lipid, protein and bacteria, including surface modification, plasma treatment, and optimization of lens material formulation, etc. To date, however, none of the methods are able to prevent all three types of depositions on contact lens due to different properties between these biomolecules and/or bacteria that require drastically different treatment to resist their deposition on the contact lenses. For example, hydrophobic surfaces may resist the adsorption of proteins but attract lipids. Another issue for current contact lens surface modification is polymer chain rearrangement, a process that changes surface properties of contact lenses over time, thus contributing to the failure of contact lenses to prevent the adsorption of biomolecules.

There is a recognized need, therefore, for a novel design of a contact lens drug delivery system and/or for methods for contact lens treatment that is able to resist the deposition of lipids, proteins and bacteria and avoid the rearrangement of the polymer chains on the contact surface. The present invention fulfills this longstanding need and desire in the art.

SUMMARY OF THE INVENTION

The present invention is directed to a fluorinated compound effective as an ophthalmic drug and/or to reduce deposition of lipids, proteins and bacteria on a contact lens. The compound has the chemical structure:

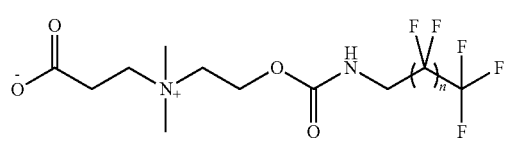

wherein n is 0 or greater, or the chemical structure

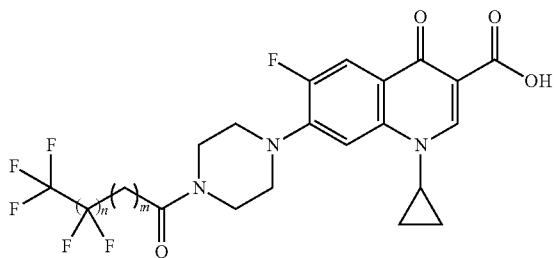

wherein m and n are 0 or greater. The present invention is also directed to an amino acid, a soluble polymer, an oligo(ethylene glycol), a poly(ethylene glycol), or a carbohydrate each fluorinated with a perfluorocarbon having the chemical structure:

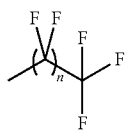

wherein n is 0 or greater.

The present invention also is directed to an ophthalmic drug delivery system comprising a contact lens embedded with at least one of the fluorinated compounds having structures described herein. The present invention is directed to a related ophthalmic drug delivery system further comprising a saline solution rinse.

The present invention is directed further still to a method for delivering an ophthalmic drug to a subject for treating an ophthalmologic associated condition. The method comprises placing the contact lens of the ophthalmic drug delivery system described herein onto an eye of the subject. The at least one fluorinated compounds are delivered to the eye thereby treating the opthalmologic-associated condition. The present invention is directed to a related method further comprising rinsing the contact lens prior to placing it onto the eye.

The present invention is directed further still to a kit to reduce deposition of lipids, proteins and bacteria on a contact lens. The kit comprises a solution of the fluorinated compounds as described herein and instructions to use the kit. The present invention is directed to a related kit further comprising a saline solution rinse. The present invention is directed to another related kit further comprising a sterile and sealable vial for holding the solution of fluorinated compound(s).

The present invention is directed further still to a method for modifying a contact lens to deliver drugs and/or to reduce deposition of lipids, proteins, and bacteria on a contact lens. The method comprises the steps of drying the contact lens, incubating the lens with one or more fluorinated compounds in a medium and rinsing the lens.

The present invention is directed further still to a modified contact lens produced by the method described herein.

The present invention is directed further still to a method for incorporating ophthalmic drugs and/or for reducing the deposition of lipids, proteins, and bacteria on a contact lens. This method comprises the steps of producing the contact lens, incubating the contact lens in a solution of a fluorinated zwitterionic compound and/or a fluorinated ophthalmic drug compound and rinsing the contact lens. The present invention is directed to a related method further comprising storing the contact lens.

The present invention is directed further still to a method for maintaining transparency in a contact lens. The method comprises the steps of applying a fluorinated zwitterionic compound and/or a fluorinated antibacterial compound in a medium to the contact lens and rinsing the contact lens.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 2. also shows the structure of fluorinated ciprofloxacin compounds 8-11 (F-Cip 1-4) and compound 12 (Cip).

FIG. 4A shows Comfilcon A lens transmission between 400 nm and 700 nm after loading with compound 8 (F-Cip1) and compound 12 (Cip). FIG. 4B lens transparency within a wavelength range of 220-800 nm in Comfilcon A lenses loaded with F-Cip1, F-Cip2, Cip. Transmission through unloaded fresh lens is shown for comparison.

FIG. 5A illustrates the amount of compound 6 released over 16 h at a solution exchange rate of 1 mL/h. FIG. 5B illustrates the amount of compound 7 released over 8 h at a solution exchange rate of 1 mL/h. FIG. 5C illustrates the amount of compound 6 released over 360 h at a solution exchange rate of 6 mL/h. FIG. 5D illustrates the amount of compound 7 released over 120 h at a solution exchange rate of 6 mL/h. Data are expressed as mean±SD from three or more independent experiments. FIG. 5E shows release of F-Cip1 (compound 8), F-Cip2 (compound 9) and Cip (compound 12) from Comfilcon A lenses over a course of 8 h at a solution exchange rate of 1 mL/h. Data are expressed as mean±SD from three or more independent experiments.

FIG. 9A shows cytotoxicity of compounds 8 and 9 and compound 12 (control) against human telomerase corneal epithelial cells (hTCEpi) at a series of concentrations. Benzalkonium chloride (BAC) is used as positive control. Data are expressed as mean±SD from three independent experiments. FIG. 9B shows cytotoxicity of compounds 8 and 9 and compound 12 (control)-loaded Comfilcon A lenses against human telomerase corneal epithelial cells (hTCEpi). Data are mean±SD from three independent experiments.

DETAILED DESCRIPTION OF THE INVENTION

Figure 1:
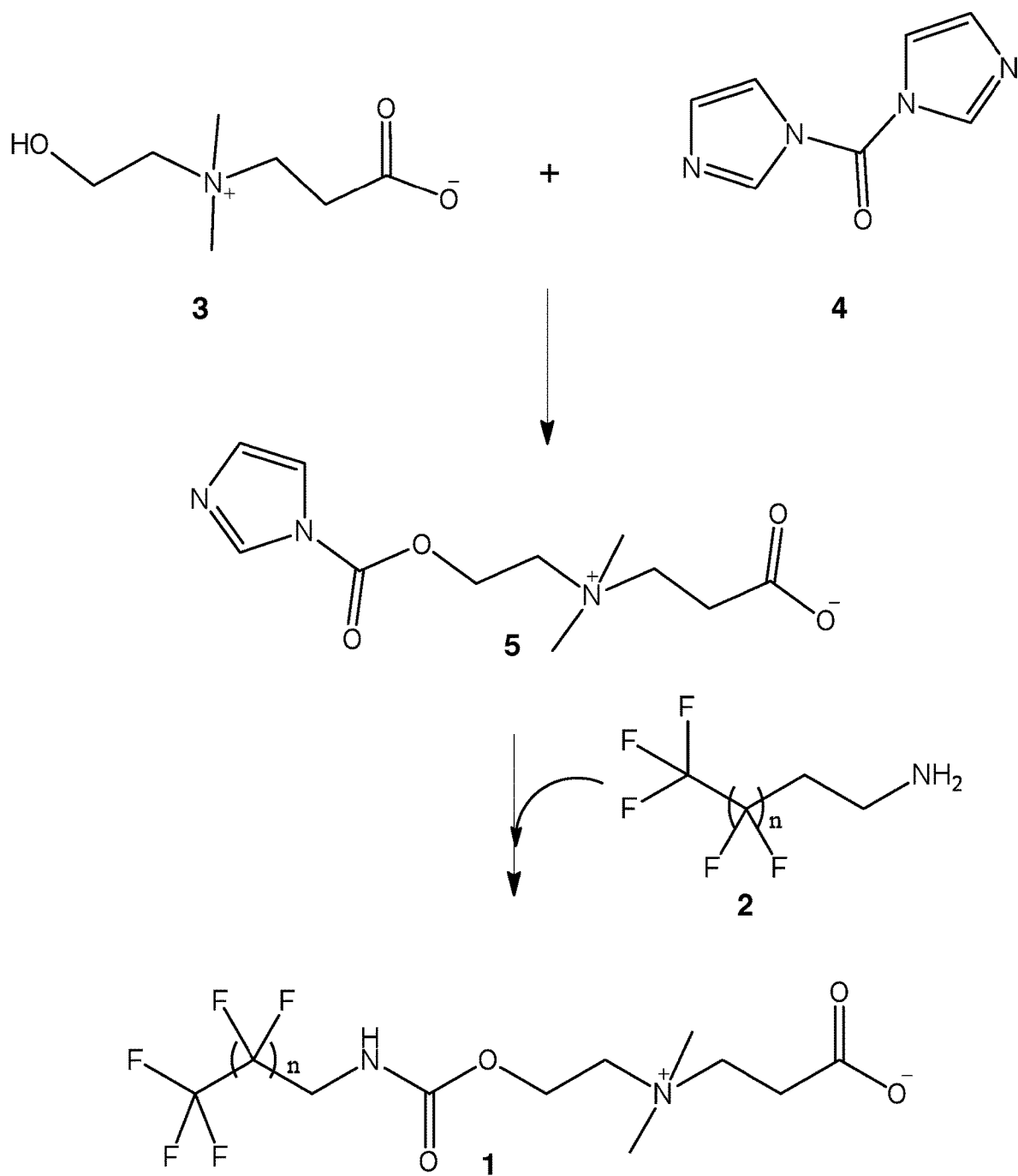
FIG. 1 shows the synthesis scheme for fluorinated Compound 1. Compounds 3 and 4 are used to produce compound 5. Then compounds 5 and 2 are combined at the molar ratio of 1:1 produce the fluorinated zwitterionic compound 1.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "blister pack" refers to a plastic, bubble-like pocket to store contact lens. Blister packs typically have a lidding seal of aluminum foil.

In one embodiment of the present invention there is provided a fluorinated compound effective as an ophthalmic drug and/or to reduce deposition of lipids, proteins and bacteria on a contact lens having the chemical structure:

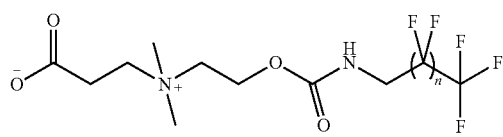

where n is 0 or greater; or

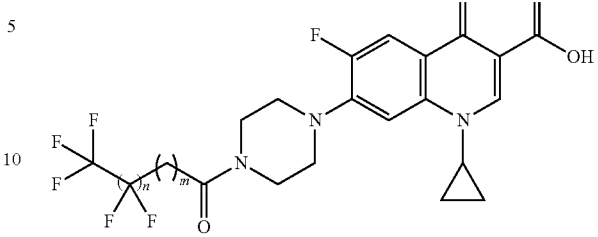

wherein n is 0 or greater and m is 0 or greater. Representative examples of useful fluorinated compounds include but are not limited to compound 8, compound 9, compound 10 or compound 11.

Alternative compounds are amino acids, a soluble polymer, an oligo(ethylene glycol), a poly(ethylene glycol), or a carbohydrate each fluorinated with a perfluorocarbon having the chemical structure:

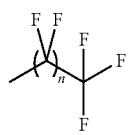

where n is 0 or greater. These compounds may be incorporated singly or in combination with each other and/or with the described fluorinated zwitterionic compounds.

The fluorinated chain lengths may be increased and the surface density of the zwitterionic groups may be adjusted. This can maximize the resistance of the contact lens to lipids, proteins, and microorganisms and the time span for which the molecules are in contact with the lenses. As the tear film is a complex system of lipids, proteins, enzymes, etc., the long-term interactions between the modified contact lenses and the tear film could possibly detach those molecules attached to the contact lenses, leading to loss of resistance of the contact lens to the tear film components (lipids, proteins) as well as microorganisms thereby making these contact lenses comfortable to wear. Optimizing the chain length can strengthen the interaction between the fluorinated zwitterionic molecules and the contact lenses, resulting in higher surface density and a longer time span that the molecules stay attached on the contact lenses.

In another embodiment of the present invention there is provided an ophthalmic drug delivery system comprising a contact lens embedded with at least one of the fluorinated compounds having structures shown above. Further to this embodiment the ophthalmic drug delivery system further comprises a saline solution rinse.

In yet another embodiment of the present invention, there is provided a method for delivering an ophthalmic drug to a subject for treating an opthalmologic-associated condition, comprising placing the contact lens of the ophthalmic drug delivery system as described supra onto an eye of the subject, where the at least one fluorinated compounds are delivered to the eye thereby treating the opthalmologic-associated condition. In a further embodiment the method comprises rinsing the contact lens prior to the placing step. In both embodiments the opthalmologic-associated condition may be an infection, glaucoma, inflammation, an allergy, or pain.

In yet another embodiment of the present invention there is provided a kit to incorporate ophthalmic drugs and/or to reduce deposition of lipids, proteins and bacteria on a contact lens, comprising a solution of the fluorinated zwitterionic compound or fluorinated ophthalmic drugs as described supra or an amino acid, a soluble polymer, an oligo (ethylene glycol), a poly(ethylene glycol), or a carbohydrate each fluorinated with a perfluorocarbon having the chemical structure:

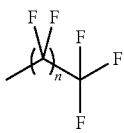

where n is 0 or greater or a combination thereof; and instructions to use the kit.

Further to this embodiment, the kit comprises a saline solution rinse. In another further embodiment, the kit comprises a sterile and sealable vial for holding the solution. In all embodiments, the solution may comprise a saline or an organic solvent. Preferably, the saline is phosphate buffered saline, saline, contact lens storage solution, and contact lens cleaning solution and the organic solvent is tetrahydrofuran, ethanol, or isopropanol.

In another embodiment of the present invention, there is provided a method for modifying a contact lens to deliver drugs and/or to reduce the deposition of lipids, proteins, and bacteria on a contact lens that contains fluorine, comprising the steps of drying the contact lens; incubating the contact lens with a medium containing a one or more fluorinated compounds; and rinsing the contact lens. In this embodiment, a representative incubating medium is a buffer. Representative buffers include, but are not limited to, phosphate buffered saline, saline, contact lens storage solution, and contact lens cleaning solution. Alternatively, a useful medium is an organic solvent. Representative organic solvents include, but are not limited to, tetrahydrofuran, ethanol, and isopropanol.

Generally, the contact lens is incubated for an amount of time necessary to incorporate the fluorinated compound(s) for drug delivery and/or reducing the deposition of lipids, proteins, and bacteria on a contact lens. Preferably, the contact lens is incubated for about 4 hours to about 24 hours, although a person having ordinary skill in this art would readily recognize that the incubation time could be as short as seconds, or as long as its entire shelf life, depending on the method utilized to do the job. The incubation is preferably performed at room temperature. In this embodiment, the method can prevent the polymer chain rearrangement of the contact lens and further, maintain transparency of the contact lens, provide ophthalmic drugs for delivery and make the contact lens resistant to microbial agents after incubation.

Particularly, the fluorinated compound is a fluorinated zwitterionic compound having the chemical structure

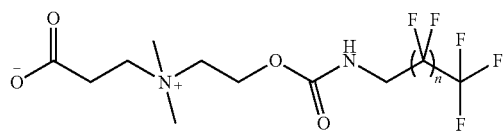

where n is 0 or greater, a fluorinated ophthalmic drug compound having the chemical structure

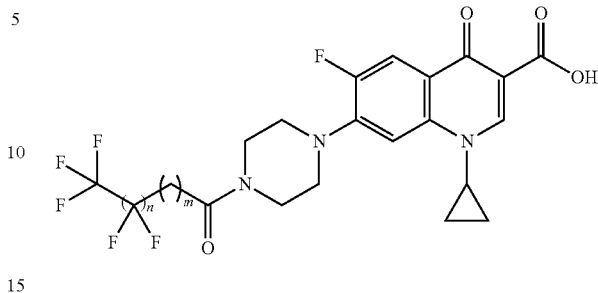

wherein n is 0 or greater and m is 0 or greater; or other fluorinated ophthalmic drugs, an amino acid, a soluble polymer, an oligo(ethylene glycol), a poly(ethylene glycol), or a carbohydrate each fluorinated with a perfluorocarbon having the chemical structure:

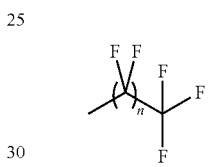

wherein n is 0 or greater. A representative fluorinated ciprofloxacin compound may be compound 8 or compound 9. For example, the fluorinated ciprofloxacin has a value of 2 for n and a value of 0 for m and has the structure of compound 8 shown in FIG. 2, wherein incubating the contact lens with a solution containing this compound makes the lens resistant to microbial agents. Alternatively, the fluorinated ciprofloxacin has a value of 3 for n and a value of 0 for m and has the structure of compound 9 shown FIG. 2, wherein incubating the contact lens with a solution containing this compound makes the lens resistant to microbial agents. Alternatively, the fluorinated ciprofloxacin has a value of 5 for n and a value of 0 for m with structure of compound 10 shown FIG. 2, or, a value of 1 for n and a value of 2 for m having the structure of compound 11 shown FIG. 2, wherein incubating the contact lens with a solution containing either compound makes the lens resistant to microbial agents.

In a related embodiment of the present invention, there is provided a modified contact lens produced by the method as described supra.

In yet another embodiment of the present invention, there is provided a method for incorporating ophthalmic drugs and/or for reducing the deposition of lipids, proteins, and bacteria on a contact lens in a manufacturing process, comprising the steps of producing the contact lens; incubating the contact lens in a solution of a fluorinated zwitterionic compound and/or a fluorinated ophthalmic drug compound; and rinsing the contact lens. Further to this embodiment the method comprises storing the contact lens.

In both embodiments the fluorinated compound may be a fluorinated zwitterionic compound having the chemical structure

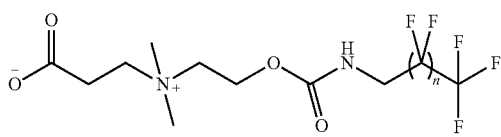

wherein n is 0 or greater. Alternatively, in both embodiments the fluorinated ophthalmic drug compound has the chemical structure:

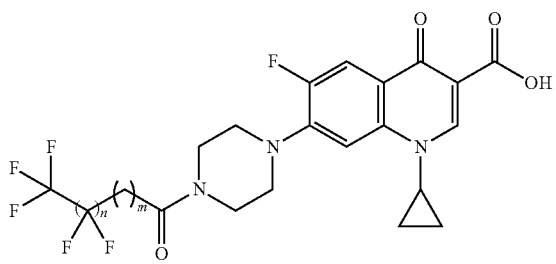

wherein n is 0 or greater and m is 0 or greater as described supra.

In both embodiments, the solution may comprise phosphate buffered saline or tetrahydrofuran, ethanol or isopropanol. In addition, the contact lens may be incubated about 4 hours to about 24 hours.

In yet another embodiment of the present invention, there is provided a method for maintaining transparency in a contact lens, comprising the steps of applying a fluorinated zwitterionic compound and/or a fluorinated antibacterial compound in a medium to the contact lens; and rinsing the contact lens. In this embodiment the fluorinated zwitterionic compound or a fluorinated antibacterial compound, for example, ciprofloxacin are as described supra. In this embodiment the medium may comprise phosphate buffered saline or tetrahydrofuran, ethanol or isopropanol. Typically, the fluorinated compounds may be applied to the contact lens for about 4 hours to about 24 hours.

In yet another embodiment of the present invention, there is provided a method for increasing a level of comfort and safety of a contact lens for a user thereof, comprising the steps of incubating the contact lens in a medium comprising a fluorinated zwitterionic compound and/or a fluorinated antibacterial compound to reduce the deposition of lipids, proteins, and bacteria thereon; and rinsing the contact lens. In this embodiment the fluorinated zwitterionic compound or the fluorinated antibacterial compound and the medium are as described supra. Also, the contact lens may be rinsed after about 4 hours to about 24 hours.

Provided herein are methods, fluorinated compounds, including fluorinated zwitterionic compounds and fluorinated ophthalmic drug compounds, and kits comprising the same for incorporating the ophthalmic drugs into contact lenses and/or for increasing the resistance to lipids, proteins, and bacteria on the surface of contact lenses. The increased resistance of the contact lens prevents loss of transparency in a contact lens, increases a level of comfort and safety of a contact lens for a user or wearer thereof and increases resistance to microbial or bacterial activity.

These methods can be used for any contact lens containing fluorine, such as, but not limited to Comfilcon A and Enfilcon A contact lenses. Particularly, the fluorinated compounds are fluorinated zwitterionic compounds such as shown synthesized using the scheme in FIG. 1 or a fluorinated anti-bacterial or anti-microbial agent, such as, fluorinated ciprofloxacin derivatives as shown in FIG. 2, or other fluorinated ophthalmic drug compound. The methods and fluorinated compounds provided herein are used as a final step of an industrial manufacturing process for contact lens production or as a post-production step initiated by a user or wearer of the contact lens. In a packing procedure the medium or solution comprising the fluorinated compounds may be stored in a blister pack for example or contained as an additive in the traditional contact lens cleaning solution for daily usage. Thus, also provided is a modified contact lens produced to contain or incorporate one or more of the described fluorinated compounds.

Particularly, the zwitterionic compounds attach to the fluorinated molecules in the contact lenses via a strong and specific fluorous attraction. The fluorinated compounds are neither water-friendly nor oil-friendly. A layer applied, coated or disposed on the outermost layer of the contact lens via fluorous attraction prevents the lipid and protein deposition. Also, when attached to the contact lenses, the zwitterionic heads of the compounds on the outer layer of the contact lenses and the fluorinated chains are embedded in the contact lens. The polymer chain rearrangement may be minimized since the fluorinated carbon chains are neither hydrophilic nor hydrophobic. The zwitterionic heads of the compounds prevent the deposition of microorganisms.

Alternative compounds are amino acids, a soluble polymer, an oligo(ethylene glycol), a poly(ethylene glycol), or a carbohydrate each fluorinated with a perfluorocarbon having the chemical structure:

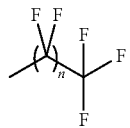

wherein n is 0 or greater. These compounds may be incorporated singly or in combination with each other and/or with the described fluorinated zwitterionic compounds.

The fluorinated chain lengths may be increased and the surface density of the zwitterionic groups may be adjusted. This can maximize the resistance of the contact lens to lipids, proteins, and microorganisms and the time span for which the molecules are in contact with the lenses. As the tear film is a complex system of lipids, proteins, enzymes, etc., the long-term interactions between the modified contact lenses and the tear film could possibly detach those molecules attached to the contact lenses, leading to loss of resistance of the contact lens to the tear film components (lipids, proteins) as well as microorganisms thereby making these contact lenses comfortable to wear. Optimizing the chain length can strengthen the interaction between the fluorinated zwitterionic molecules and the contact lenses, resulting in higher surface density and a longer time span that the molecules stay attached on the contact lenses.

A representative incubating medium is a buffer. Representative buffers include, but are not limited to, phosphate buffered saline, saline, contact lens storage solution, and contact lens cleaning solution. Alternatively, a useful medium is an organic solvent. Representative organic solvents include, but are not limited to, tetrahydrofuran, ethanol, and isopropanol. Tetrahydrofuran, may be used to replace phosphate buffered saline to dissolve the fluorinated zwitterionic compound since the solubility of the fluorinated zwitterionic compound may become limited in phosphate buffered saline depending on the length of fluorinated carbon chain.

The fluorinated compounds also may comprise a fluorinated antibacterial, anti-microbial or ophthalmic drug compounds which when incorporated into the contact lens via incubation or other application produces a drug delivery system in a modified contact lens that is worn by a subject or user thereof. The modified contact lens is useful to treat an ophthalmic-associated condition, disease or disorder. These therapeutics may be incorporated with or without the fluorinated zwitterionic compounds. The therapeutics in the modified contact lens are eluted via the natural tearing action of the eye. These therapeutic ophthalmic compounds can be used to treat and/or alleviate conditions such as infection, glaucoma, inflammation, allergy, or pain associated therewith when the contact lens comprising the one or more ophthalmic therapeutics is worn in one or both eyes.

Contact lens care solutions containing the above fluorinated drug and lubricating molecules can be used for storage of commercial fluorinated contact lenses between wear. Due to the fluorous interactions, these molecules will incorporate into contact lenses and provide therapeutic or improved wear experience.

The invention thus provides a number of advantages and uses, which are described below, however, the advantages and uses are not limited by this description. Embodiments of the present invention are better illustrated with reference to the Figure(s), however, such reference is not meant to limit the present invention in any fashion. The embodiments and variations described in detail herein are to be interpreted by the appended claims and equivalents thereof.

Example 1

Synthesis of Fluorinated Molecules

Figure 2:
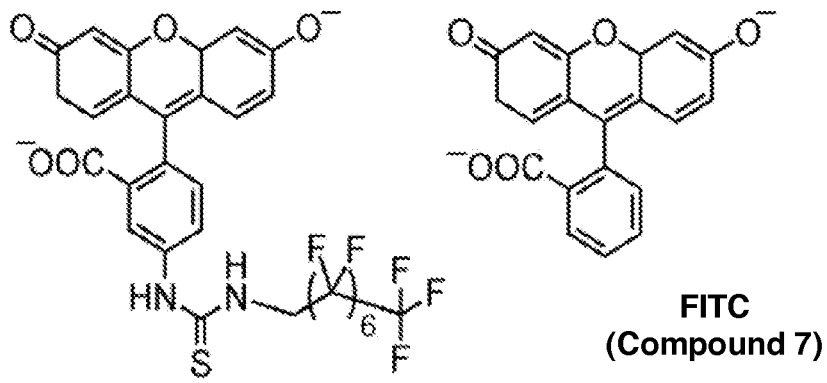
FIG. 2 shows the chemical structures of molecules tested to attach to contact lenses. A fluorescent dye tagged with a fluorinated carbon chain (FITC-$C_8F_n$) shown in FIG. 2 is used as a model compound 6 (n=5). The attachment of these compounds to the contact lenses can be easily detected and quantified by its fluorescence signal. Compound 7 (FITC) is used as negative control.
Figure 2:
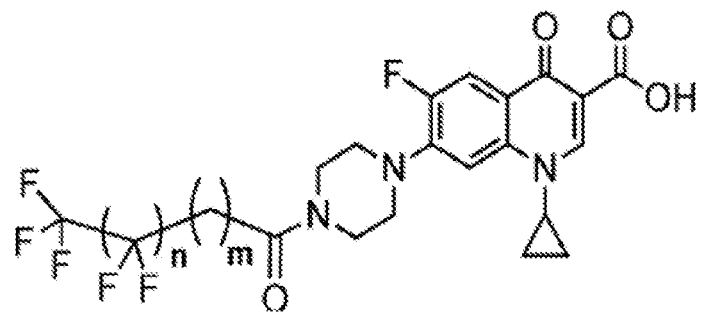
Figure 2:
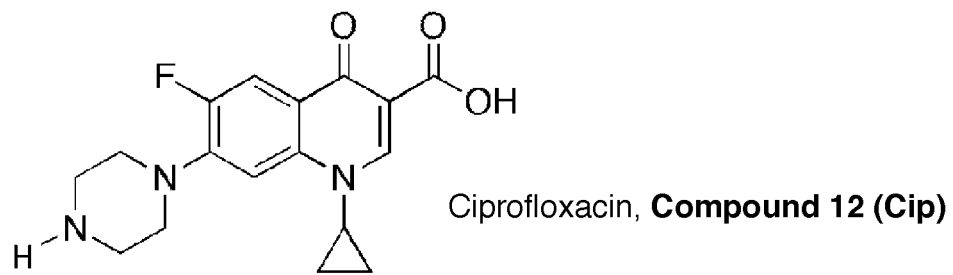

The synthetic scheme for fluorinated molecules 1 is shown in FIG. 1. For compound 2 the n in the formulation is equal to 7. Compounds 2 and 3 are used without further purification. Compounds 3 and 4 with a molar ratio of 1:1.1 are dissolved in tetrahydrofuran in a round shape flask and stirred using a magnetic stirrer at room temperature overnight. The solvent is evaporated using a rotary evaporator, and the product 5 is purified using chromatography. A mixture of 2 and 5 with a molar ratio of 1:1 is stirred at room temperature overnight followed by solvent removal and purification using chromatography. All purified compounds are characterized using mass spectroscopy and nuclear magnetic resonance (NMR).

Synthesis of Fluorinated Fluorescein

The synthesis of FITC-$C_8F_{15}$ is carried out as reported previously. Briefly, 15.57 mg of fluorescein isothiocyanate (FITC) is dissolved in 10 mL of ethanol. Then, 10 mL of 1H, 1H-perfluorooctylamine (2 mM in ethanol) is added drop wise at room temperature with stirring. The solution is stirred at room temperature for 24 hours. The solvent is then evaporated under reduced pressure, and the residue purified by silica gel flash chromatography (ethyl acetate/Methanol 9/1), to give FITC—$C_8F_{15}$ (22 mg, 93% yield) as a green powder (FIG. 2). The structure of FITC-$C_8F_{15}$ is verified by NMR and MALDI-TOF-MS m/z: [M]$^+$ to have the formula, $C_{29}H_{17}F_{15}N_2O_5S$, and a formula weight of 790.06219.

$^1$H NMR (500 MHz, acetone-d6) δ 9.05 (s, 2H), 7.98-7.89 (m, 2H), 7.26 (dd, J=8.1, 7.0 Hz, 1 H), 6.75 (d, J=2.5 Hz, 2H), 6.72 (d, J=4.0 Hz, 1H), 6.70 (d, J=3.5 Hz, 1H), 6.65-6.64 (m, 1H), 6.63 (dt, J=4.9, 1.8 Hz, 1H), 4.75 (dtd, J=48.0,16.4, 6.2 Hz, 2H), 4.47 (q, J=7.2 Hz, 1H). $^{13}$C NMR (126 MHz, Acetone-d6) δ 184.39, 169.11, 169.07, 160.30, 153.35, 153.32, 153.28, 149.98, 146.63, 141.81, 131.30, 130.17, 130.13, 130.09, 128.40, 125.88, 125.17, 125.12, 124.75, 119.22, 119.07, 117.36, 116.63, 113.30, 111.65, 111.58, 111.55, 103.33, 55.44. $^{19}$F NMR (471 MHz, CDCl$_3$) δ −81.44-81.64 (m, 3F), −117.09-117.92 (m, 2F), −122.23 (s, 2F), −122.46 (s, 2F), −123.18 (s, 2F), −123.94 (s, 2F), −126.63 (td, J=14.6, 6.9 Hz, 2F). MALDI-TOF-MS m/z: [M]$^+$ calculated for $C_{29}H_{17}F_{15}N_2O_5S$=790.06; found: 790.10.

Synthesis of Fluorinated Ciprofloxacin Derivatives

Ciprofloxacin (250 mg, 0.75 mmol) and triethylamine (139 µL, 1 mmol) is stirred in anhydrous methylene chloride (5 mL) at 0° C. for 15 min. Heptafluorobutyric acyl chloride (259.8 mg, 1.12 mmol) is added drop wise to the mixture and the reaction is protected under nitrogen atmosphere. The suspension is stirred at room temperature for 12 hours, following which, the volatile components are removed under reduced pressure. The residue is then purified by silica gel column chromatography to yield compound 8 (173.9 mg, 33% yield) as a white powder (FIG. 2 m=0, n=2) verified by NMR and MS (ESI) m/z: [M+H]$^+$ to have the formula $C_{21}H_{18}F_8N_3O_4$ and a formula weight of 528.09.

$^1$H NMR (500 MHz, CDCl$_3$) d 8.73 (s, 1H), 8.01 (d, J=12.7 Hz, 1H), 7.38 (d, J=7.0 Hz, 1H), 3.96 (dd, J=8.9, 4.7 Hz, 4H), 3.56 (s, 1H), 3.45-3.36 (m, 4H), 1.42 (q, J=6.6 Hz, 2H), 1.21 (t, J=5.0 Hz, 2H). $^{13}$C NMR (126 MHz, CDCl$_3$) δ 177.15, 166.83, 156.47, 154.70, 152.70, 147.81, 145.03, 139.05, 120.82, 112.95, 112.77, 108.40, 105.50, 50.17, 49.42, 45.95, 43.55, 35.49, 8.43. $^{19}$F NMR (470 MHz, CDCl$_3$) δ 79.58 (t, J=9.5 Hz, 3F), −111.46-111.53 (m, 2F), −121.14-121.21 (m, 2F), −125.51-125.57 (m, 2F). MS (ESI) m/z: [M+H]$^+$ calculated for $C_{21}H_8F_8N_3O_4$=528.12; found 528.09.

Ciprofloxacin (250 mg, 0.75 mmol) and triethylamine (139 µL, 1 mmol) are stirred in anhydrous methylene chloride (5 mL) at 0° C. for 15 min. Perfluoropentanoyl chloride (315.8 mg, 1.12 mmol) is added drop wise into the mixture and the reaction is protected under nitrogen atmosphere. The suspension is stirred at room temperature for 12 hours, following which, the volatile components are removed under reduced pressure and the residue further purified by silica gel column chromatography to yield Compound 9 (178.9 mg, 31% yield) as a yellow powder (FIG. 2 m=0, n=3) verified by NMR and MS (ESI) m/z: [M+H]$^+$ to have the formula of $C_{22}H_{18}F_{10}N_3O_4$=578.11 and a formula weight of 578.08.

$^1$H NMR (500 MHz, Acetone-d6) δ 8.70 (s, 1H), 7.93 (d, J=13.1 Hz, 1H), 7.79 (d, J=7.4 Hz, 1H), 4.06-3.94 (m, 4H), 3.88 (dd, J=7.1, 3.5 Hz, 1H), 3.61-3.52 (m, 4H), 1.48 (d, J=6.0 Hz, 2H), 1.39-1.30 (m, 2H). $^{13}$C NMR (126 MHz, Acetone-d6) δ 177.89, 166.64, 156.59, 155.42, 153.44, 149.00, 145.87, 145.79, 140.35, 130.20, 129.37, 127.17, 120.96, 112.31, 112.12, 108.59, 107.80, 50.73, 50.05, 46.41, 44.04, 36.61, 8.49. $^{19}$F NMR (471 MHz, CDCl$_3$) δ 80.86 (t, J=9.8 Hz, 3F), δ −110.94 (t, J=12.2 Hz, 2F), _121.09 (dd, J=12.7, 6.9 Hz, 2F), _121.86 (dddd, J=13.4, 10.0, 6.7, 3.4 Hz, 2F), 124.50-24.62 (m, 2F). MS (ESI) m/z: [M+H]$^+$ calculated for $C_{22}H_{18}F_{10}N_3O_4$=578.11; found 578.08.

Ciprofloxacin (250 mg, 0.75 mmol) and triethylamine (139 µL, 1 mmol) are stirred in anhydrous methylene chloride (5 mL) at 0° C. for 15 min. The perfluoroheptanoic acyl chloride (427.8 mg, 1.12 mmol) is added drop wise in to the mixture and the reaction is protected under nitrogen atmosphere. The suspension is stirred at room temperature for 12 hours, following which, the volatile components are removed under reduced pressure and the residue further purified by silica gel column chromatography to yield compound 10 (202 mg, 40% yield) as a pale yellow powder.

$^1$H NMR (500 MHz, CDCl$_3$) δ 8.63 (s, 1H), 7.86 (d, J=12.7 Hz, 1H), 7.34 (d, J=7.0 Hz, 1H), 3.93-3.71 (m, 4H), 3.61-3.51 (m, 1H), 3.47-3.28 (m, 4H), 2.68 (dd, J=9.6, 6.2 Hz, 2H), 2.49 (ddd, J=17.6, 14.4, 7.8 Hz, 2H), 1.40 (q, J=6.7 Hz, 2H), 1.20 (q, J=6.5 Hz, 2H). $^{13}$C NMR (126 MHz, CDCl$_3$) δ 176.91, 168.77, 167.31, 154.64, 152.64, 147.63, 145.46, 145.37, 139.06, 120.04, 119.98, 112.50, 112.31, 107.84, 105.24, 49.89, 49.36, 45.23, 41.67, 35.53, 26.57, 26.40, 26.23, 24.38, 8.32. $^{19}$F NMR (470 MHz, CDC13) δ 80.62 (t, J=9.9 Hz, 3F), -110.68 (t, J=13.4 Hz, 2F), -120.60 (s, 2F), -121.00 (dd, J=15.2, 8.0 Hz, 2F), -121.14 (dd, J=12.7, 6.9 Hz, 2F), -122.67 (s, 2F), -125.81-125.92 (m, 2F). MS (ESI): [M+H]$^+$ calculated for C$_{22}$H$_{22}$F$_6$N$_3$O$_4$=506.1, Found 506.2.

Ciprofloxacin (250 mg, 0.75 mmol) and triethylamine (139 μL, 1 mmol) are stirred in anhydrous methylene chloride (5 mL) at 0° C. for 15 min. The 4,4,5,5,5-pentafluoropentanoic acyl chloride (235.2 mg, 1.12 mmol) is added drop wise in to the mixture and the reaction is protected under nitrogen atmosphere. The suspension is stirred at room temperature for 12 hours, following which, the volatile components are removed under reduced pressure and the residue further purified by silica gel column chromatography to yield compound 11 (203 mg, 30% yield) as a yellow powder.

$^1$H NMR (500 MHz, CDCl$_3$) δ 8.77 (s, 1H), 8.05 (d, J=12.7 Hz, 1H), 7.38 (d, J=6.6 Hz, 1H), 3.96 (d, J=11.8 Hz, 4H), 3.55 (s, 1H), 3.40 (s, 4H), 1.42 (d, J=5.9 Hz, 2H), 1.22 (s, 2H). $^{13}$C NMR (126 MHz, CDCl$_3$) δ 177.23, 166.85, 156.57, 154.73, 152.73, 147.87, 144.95, 139.08, 121.04, 120.98, 113.10, 112.92, 111.37, 110.84, 110.62, 108.56, 105.50, 50.26, 49.45, 46.00, 43.62, 35.48, 8.45. $^{19}$F NMR (470 MHz, CDC13) δ -85.32 (s, 3F), -118.30 (t, J=18.5 Hz, 2F), -121.05-121.10 (m, 2F). MS (ESI): [M+H]$^+$ calculated for C$_{24}$H$_{18}$F$_{14}$N$_3$O$_4$=678.1, Found 678.1.

Example 2

Modification of Contact Lens with Fluorinated Molecules

Commercial Comfilcon A lenses are removed from blister packs, and blotted gently to remove excess solution. Lenses are placed individually into glass vials containing the synthesized fluorinated molecules in phosphate buffered saline or other saline (20 μM) and incubated for 4 hours to 24 hours at room temperature. At the end of incubation, lenses are washed with PBS or saline three times, and blotted dry or air dried for further experiments. As the fluorinated carbon chain length increases, the solubility of these molecules will become limited. If necessary, organic solvent is used for better solubility.

Example 3

Quantification of Attached Molecules and Characterization of the Modified Contact Lens To determine the amount of fluorinated molecules attached onto contact lenses, perfluorocarbon solvent is used to dissolve the attached molecules out, and liquid chromatography-Mass Spectrometry is used to identify and quantify the amount. Specifically, modified lenses are placed into glass vials containing 1 mL perfluorocarbon solvent and sonicated for several minutes at room temperature. This process is repeated 3 times, and then all the solution is collected and combined into a flask followed by evaporation using a rotary evaporator. The residue in the flask is dissolved in 100 μL of acetonitrile and injected into liquid chromatography-Mass Spectrometry with acetonitrile as mobile phase. The molecule is identified from Mass Spectrometry spectrum using molecular ion peak and the quantity is measured from the chromatography peak area.

X-ray photoelectron spectroscopy (XPS) is used to determine the surface properties and atomic concentrations of C1s, N1s, O1s, F1s, Si2p of five types of commercial contact lenses, Comfilcon A, Narafilcon A, Lotrafilcon B, Ocufilcon D, and Delefilcon A, and contact angle are measured by goniometer. Briefly, lenses are dried in air and cut into pieces of ~5×5 mm$^2$. Each piece is glued onto a stainless steel holder and loaded into a PHI 5700 X-ray photoelectron spectrometer, equipped with a monochromatic AlKα X-ray source (hv=1486.7 eV) at a take-off angle (TOA) of 45° from the film surface. XPS confirms the presence of fluorinated molecules at the surface of contact lenses by detecting fluorine signals. The advancing and receding contact angles are measured using a Rame-Hart goniometer. At least four drops of probe liquid are measured for each sample.

Example 4

Statistical Analysis

Data are expressed as mean±SD. Where applicable, statistical analysis is performed using one-way or two-way ANOVA followed by Tukey's test where significance is found with p<0.05.

Adsorption of Lipids, Proteins and Microorganisms onto Modified Contact Lenses

The adsorption of lipids such as phosphatidylcholine and cholesterol oleate, proteins such as lysozyme and albumin, and microorganisms such as *Pseudomonas aeruginosa* and *Staphylococcus aureus* are tested on contact lenses modified above.

Loading of Molecules into Commercial Contact Lenses

A list of the commercial contact lenses tested is presented in Table 1. All lenses are air dried and weighed. The weights of Comfilcon A, Narafilcon A, Lotrafilcon B, Ocufilcon D and Delefilcon A lenses were 16.3±0.3, 15.6±0.1, 20.7±0.3, 15.7±0.2, and 21.5±0.4 mg, respectively. Compounds used including FITC-F, FITC, Ciprofloxacin (Cip, compound 12), fluorous-tagged ciprofloxacin (F-Cip1-4) are shown in FIG. 2.

Briefly, commercial lenses are individually immersed in wells of a 24 well plate, each containing 1 mL PBS solution of FITC-F (15.6 mM), FITC (15.6 mM), Cip (100 mM) or F-Cip (100 mM), and incubated for 18 h. Then the lenses are washed with PBS three times for 5 min each. All incubation and wash solutions are collected and the amount of each compound is quantified by spectrophotometry. Standard curves are generated with seven standard samples with known concentrations for each individual compound of interest. Specifically, fluorescent compounds FITC and FITC-F are quantified by fluorescence emission at 520 nm (lex.485 nm), and Cip and F-Cip are quantified by absorbance at 275 nm. The amount of each compound in the above collected solutions is then measured with the standard curve. The amount of the compound incorporated into lenses was determined by subtracting the amount in solution from the total amount added initially.

Lens Transparency After Modification

To determine the transparency of fresh and modified Comfilcon A contact lenses using light transmission, contact lenses are cut into small disks with a diameter of 6 mm and placed into wells of a UV-transparent 96-well plate, and a wavelength scan from 220 to 800 nm is conducted using a plate reader (BMG LabTech FLUOstar Omega plate reader, Germany).

Time Course Release of Individual Compounds from Contact Lenses

The modified Comfilcon A lenses are placed into individual wells of a 24 well plate with 1 mL PBS in each well at room temperature. The PBS solution is replaced with fresh PBS every hour for up to 8 h or 15 h, or every 10 min for 2 h or 6 h. The amount of fluorescent compound released into the collected PBS aliquots is quantified spectrophotometrically based on the above standard curve. The amount of F-Cip released into the collected PBS aliquots is quantified using LC-MS (LCQ Deca XP plus with Surveyor LC, Thermo Fisher, Waltham, Mass.) with electrospray ionization in positive ion mode. Samples (5 mL each) are loaded onto the analytical column at 200 mL/min (Kinetex XB-C18, 2.×50 mm, 2.6 mm, Phenomenex) with the following gradient: 0-3 min, 10-75% (B); 3-7.5 min, 75-91% (B). The mobile phase consists of (A) water containing 0.1% formic acid and (B) acetonitrile containing 0.1% formic acid. Mass spectrometric parameters are as follows: 250° C. capillary temperature, 45 units sheath gas, 10 units aux gas and 4.5 kV spray voltage. Selective ion monitoring (SIM) is used for detecting F-Cip 1 and 2 (compounds 8 and 9), and the quantification is based on the respective standard calibration curve. The detection limit for F-Cip 1 and 2 (compounds 8 and 9) is approximately 1.5 pg based on S/N ratios.

Antibacterial Activity of F-Cip

Laboratory strain *Pseudomonas aeruginosa* (*P. aeruginosa*) ATCC 19660 is used to test the antimicrobial activity of modified ciprofloxacin. The strain is inoculated and grown at 37° C. for 18 h. The bacterial suspension (300 mL) is added into 100 mL of nutrient broth and incubated for 2 h to reach a log growth phase. The resulting bacterial suspension is adjusted to a concentration of ~$10^7$ cfu/mL and 100 mL are placed into each well of a 96 well plate. Fifty microliters of F-Cip solution are added into the 96 well plate and incubated at 37° C. for 18 h. The inhibition of microbial growth is determined by measuring the absorbance at 620 nm. The concentration that inhibited 50% of bacterial growth (IC50) is calculated based on absorbance readings from three independent experiments.

Cytotoxicity of F-Cip and Modified Contact Lenses

Telomerase modified human corneal epithelial cells were seeded into wells of a 96 well plate with 100 mL KGM-2 medium (Lonza Ltd, Switzerland) and incubated at 37° C. until ~80% confluence. Ten microliters of compounds 8-12 are added to the wells with final concentrations of 10, 5, 2.5, 1.25, 0.63, 0.31, 0.16, 0.08, 0.04, 0.02 mM. Cells treated with 0.05% benzalkonium chloride (BAC) and without any treatment served as controls. The plate was incubated at 37° C. for 18 h, and cell viability was determined using a cell counting kit-8 assay. To determine the cytotoxicity of contact lenses, control and modified Comfilcon A lenses are cut into small disks with a diameter of 6 mm and placed individually into wells of the 96 well plate in duplicate followed by incubation at 37° C. for 18 h. All lenses are taken out, and cell viability was determined using a cell counting kit-8 assay (Dojindo Molecular Technologies, Inc. Japan).

Ex Vivo Infection Model and Antimicrobial Activity of F-Cip Loaded Contact Lenses.

Due to their similar size and anatomy with human eyes, porcine eyes have been adopted to test the effectiveness of contact lenses in ex vivo models that had a mechanism to mimic the tear turnover. Fresh porcine eyes were purchased from a commercial slaughterhouse (Sioux-Preme Packing Co., Chicago, Ill.). Upon arrival, eyelids and connective tissues are removed and the porcine eyes are sanitized using 5% penicillin/streptomycin (Sigma-Aldrich, St. Louis, Mo.) for 1 h followed by washing thrice with PBS. Six scratch wounds with a 3×3 crosshatch pattern of length about 1 cm are created on each cornea using a 27G needle. The eyes are placed into holders and 100 mL of bacterial solution containing $10^6$ CFU (see "Antibacterial activity of F-Cip" section discussed above) applied to each cornea. The eyes are left at room temperature in a biosafety cabinet for 5 h. After rinsing with 10 mL of PBS, control and modified Comfilcon A contact lenses are placed individually onto the eyes. Eyes without any lenses and eyes treated with 0.3% ciprofloxacin (Cip) solution every 15 min for 1 h served as controls. One eye without scratches but incubated with bacteria served as an additional control. A custom-made apparatus is used to flow culture medium over the surface of the porcine eyes. This apparatus consisted of a fluid reservoir containing DMEM (Life Technologies, Inc. Carlsbad, Calif.) and small diameter tubing positioned to create a flow rate of four 25 mL drops per min onto individual porcine eyes that are placed directly underneath the tube outlet. The eyes were left for 12 h, and then rinsed with 10 mL PBS. The corneas were dissected and cut into pieces using a sterile scalpel followed by homogenizing using a LabGen 125 homogenizer (Cole-Parmer, Vernon Hills, Ill.) for 1.5 min in 2 mL PBS. Five hundred microliters of the homogenate solution from each sample was added into individual tubes with 6 mL nutrient broth, and the mixtures were shaken at 250 rpm at 37° C. for 10 h. Then 100 mL of the bacterial suspension from each sample was taken out and added into a 96-well plate in triplicate, and absorbance at 620 nm was measured and plotted as percentage of bacterial growth inhibition compared to the corneas infected with bacteria but without any treatments.

Adsorption of Phosphatidylcholine and Cholesterol Oleate

The adsorption of lipids by modified contact lenses was determined using radiolabelled lipids 3H-phosphatidylcholine and 14C-cholesterol oleate detected by scintillation counting. Non-modified lenses are used as control. Modified lenses are soaked in 3H-phosphatidylcholine (0.0005 mg/mL) or 14C-cholesterol oleate (0.024 mg/mL) in phosphate buffered saline, or phosphate buffered saline alone as control. Lenses are placed individually into glass vials containing the above lipids or phosphate buffered saline and incubated for 8 h up to 24 h at 35° C. Each lens is washed with phosphate buffered saline three times, and then counted in a scintillation counter. The experiment is repeated three times, and the amount of lipids adsorbed onto modified lenses is compared with the amount of lipids adsorbed onto non-modified lenses using student's t-test.

Adsorption of Lysozyme and Albumin

The adsorption of lysozyme and albumin onto modified lenses is determined using XPS. Modified lenses or non-modified lenses are soaked in lysozyme (1.9 mg/mL) or albumin (0.2 mg/mL) in phosphate buffered saline, or phosphate buffered saline alone as control. Lenses are placed individually into glass vials containing the above proteins or phosphate buffered saline and incubated for 8 h up to 24 h at 35° C. Each lens is washed with PBS three times and vacuum-dried. The amount of proteins adsorbed onto each lens is calculated by the nitrogen signal from XPS. The amount of proteins adsorbed onto modified lenses is compared with the amount of protein adsorbed onto non-modified lenses using student's t-test.

Adsorption of *Pseudomonas aeruginosa* and *Staphylococcus aureus*

The number of bacteria adsorbed onto contact lenses was determined using fluorescently stained *Pseudomonas aeruginosa* and *Staphylococcus aureus* detected by fluorescence microscopy. Modified lenses were placed individually into glass vials containing the above bacteria (107 cfu) and incubated for 8 h up to 24 h at 35° C. Non-modified lenses were used as control. Each lens was washed with phosphate buffered saline three times, stained with hoechst, and observed using fluorescence microscopy. At least three imaging fields are randomly chosen for each lens sample. The number of bacteria adsorbed onto each lens per imaging field was counted using ImageJ software. The experiments were repeated three times and the amount of bacteria adsorbed onto modified lenses was compared with the amount of bacteria on non-modified lenses using student's t-test.

Example 5

Interaction of Fluorinated Zwitterionic Molecules with Different Types of Lenses To demonstrate the concept of using fluorous attractions to attach fluorinated molecules onto contact lenses with fluorine, a fluorinated carbon chain (FITC-$C_8F_{15}$) tagged with a fluorescent dye shown in FIG. 2 is used as a model compound. The attachment of this compound can be easily detected and quantified by its fluorescence signal. FITC is used as control. Four types of contact lenses were tested and their properties are listed in Table 1. Among these 5 types of lens materials, Comfilcon A, Lotrafilcon B and Narafilcon A are silicone hydrogel, Ocufilcon D is conventional hydrogel, and Delefilcon A is a mixture of both materials. Notably, among these 4 types of lens materials, only Comfilcon A has fluorine elements in its formulation.

solutions, which was calculated based on the fluorescence intensity for each fluorescence dye.

Figure 3:
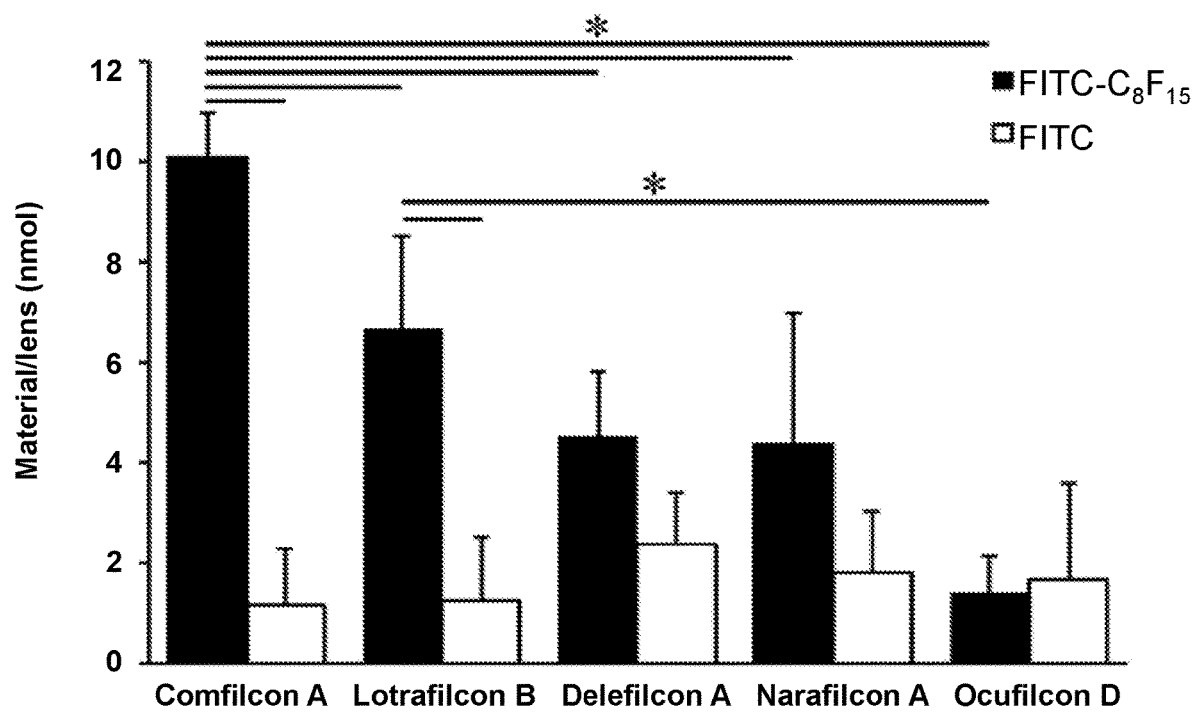
FIG. 3 illustrates the amount of compound 6 (FITC-$C_8F_{15}$) and compound 7 (FITC) loaded onto Comfilcon A, Lotrafilcon B, Delefilcon A, Narafilcon A and Ocufilcon D lenses. Data are from at least three independent experiments and are expressed as mean±SD. Two-way ANOVA is performed followed by Tukey's test where significance is found. *$p<0.05$.

As shown in FIG. 3, Comfilcon A type lenses attached the greatest amount of FITC-$C_8F_{15}$ among the lenses tested. Furthermore, for the Comfilcon A and Lotrafilcon B type lenses, the amount of FITC-$C_8F_{15}$ or FITC-$C_8F_{15}$ attached are significantly more than the amount of FITC attached (FITC-$C_8F_{15}$: Comfilcon A, 11 times and Lotrafilcon, B 6.5 times; FITC-$C_8F_{15}$: Comfilcon A, 9 times and Lotrafilcon B, 5 times). The structural difference between FITC-$C_8F_n$, and FITC is the fluorinated carbon chain (see FIG. 2 for their chemical structures). As only the Comfilcon A and Lotrafilcon B type lens has fluorinated molecules in its formulation, the above results indicated that the presence of fluorine in Comfilcon A and Lotrafilcon B type lens greatly facilitated the attachment of FITC-$C_8F_{15}$.

Example 6

Transparency of the Contact Lens After Drug Incorporation

Figure 4A:
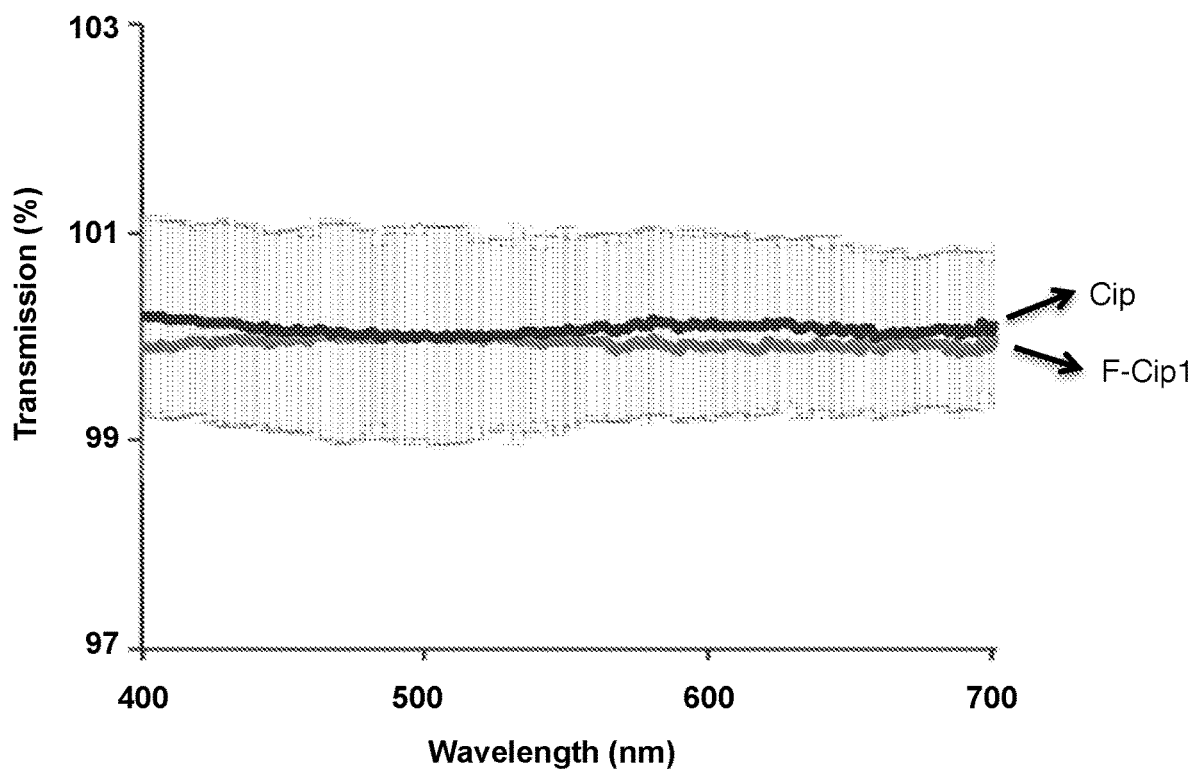
FIG. 4A-4B Illustrate contact lens transparency after incubation with F-Cip compounds.
Figure 4B:
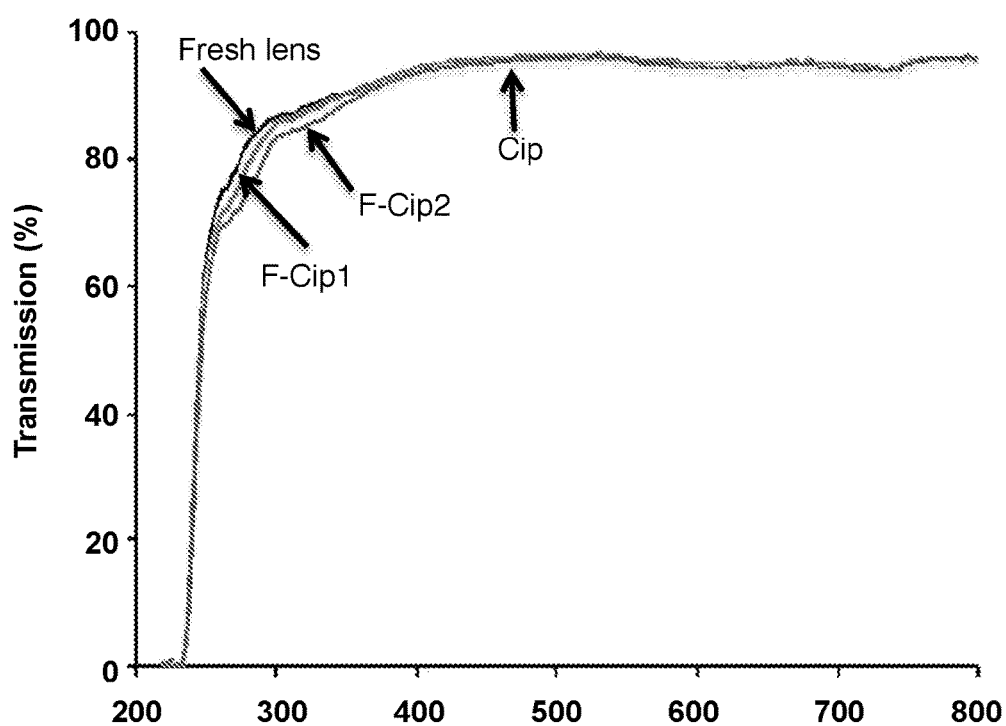

FIG. 4A illustrates the transparency of contact lenses incubated with fluorinated ciprofloxacin compound F-Cip1 and control ciprofloxacin (Cip). Transmission of modified lenses remained remarkably close to about 100% between 400 nm and 750 nm for bot Cip and F-Cip1 embedded lenses. Similarly, as illustrated in FIG. 4B, lenses embedded with Cip, F-Cip1 and F-Cip2 show transmission profiles that significantly overlap with that for a fresh unmodified lens between 200 nm and 800 nm. As reported, ciprofloxacin (Cip) loaded lenses often exhibit precipitates and lose their transparency. Therefore, the current simple method is advantageous since it has addressed previous issues of loss of transparency of Cip loaded lenses that often exhibited precipitates.

TABLE 1

Properties of Lens Types Used

| Trade Name | Biofinity | Air Optix | Biomedics 55 UV | 1-day Acuvue TrueEye | Dailies Total 1 |
|---|---|---|---|---|---|
| USAN | Comfilcon A | Lotrafilcon B | Ocufilcon D | Narafilcon A | Delefilcon A |
| Manufacturer | Cooper Vision | Alcon | Cooper Vision | Johnson & Johnson | Alcon |
| Water content % | 48 | 33 | 55 | 54 | 33 core, >80 surface |
| Material | Silicone hydrogel | Silicone hydrogel | Hydrogel | Silicone hydrogel | Silicon hydrogel core non-silicone hydrogel surface |
| Atomic conc. of surface Fl % | 3.7 | 1.05 | 0 | 0 | 0 |

Commercial lenses of the above 4 types were removed from blister packs, and blotted gently to remove excess solution. Contact lenses were placed individually into glass vials and immersed in 1 mL of FITC-$C_8F_{15}$ or FITC solution (15.6 μM in phosphate buffered saline) for 24 hours at room temperature. At the end of incubation, lenses were washed three times using phosphate buffered saline. The fluorescence of the incubation solution as well as each wash solution was measured using a BMG LabTech FLUOstar Omega plate reader, and the amount of fluorescent molecules attached onto the contact lenses is calculated as follows:

$$M_{adsorbed\ onto\ contact\ lens} = M_{total} - M_{solution}$$

where $M_{total}$ is 15.6 nmole, and $M^{solution}$ is the total amount of fluorescent molecules in the incubation solution and wash Example 7

Figure 5A:
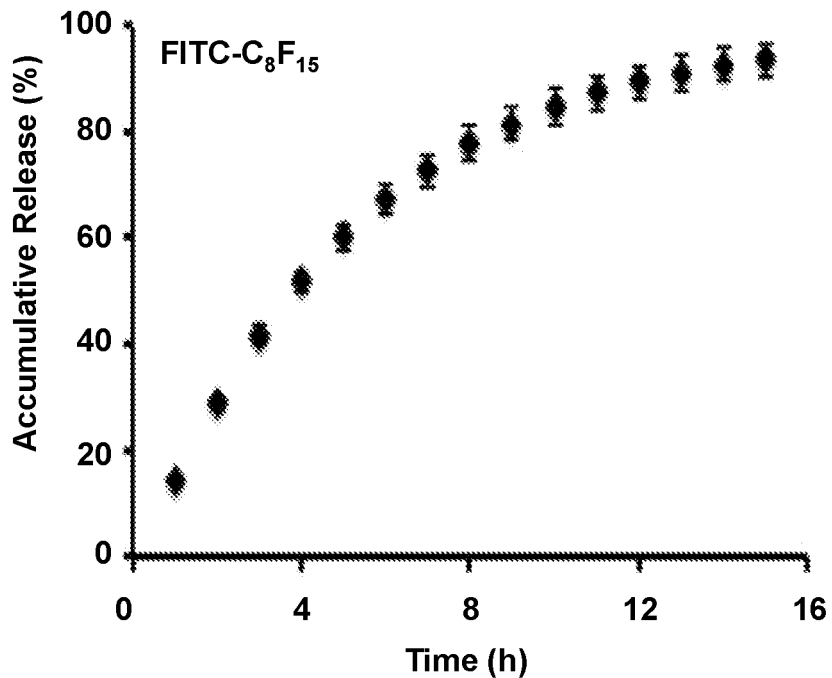
FIG. 5A-5E shows release of compounds from Comfilcon A lens.
Figure 5B:
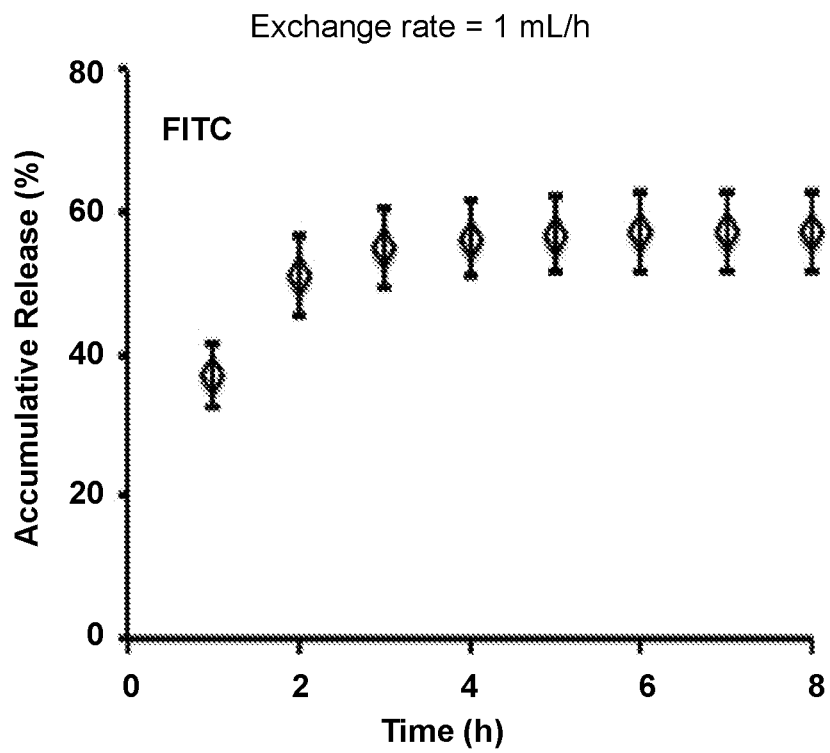
Figure 5C:
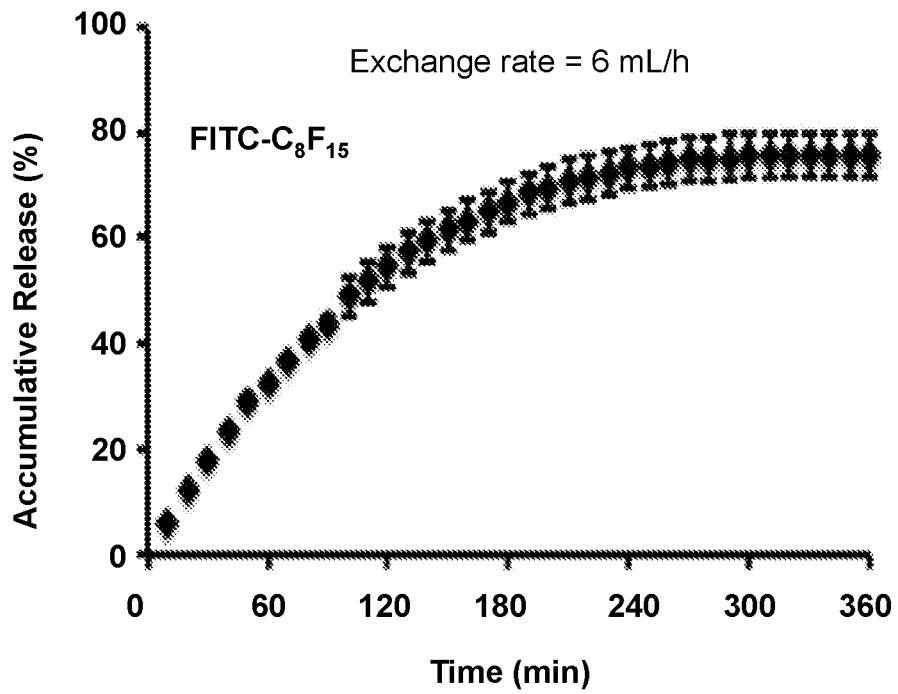
Figure 5D:
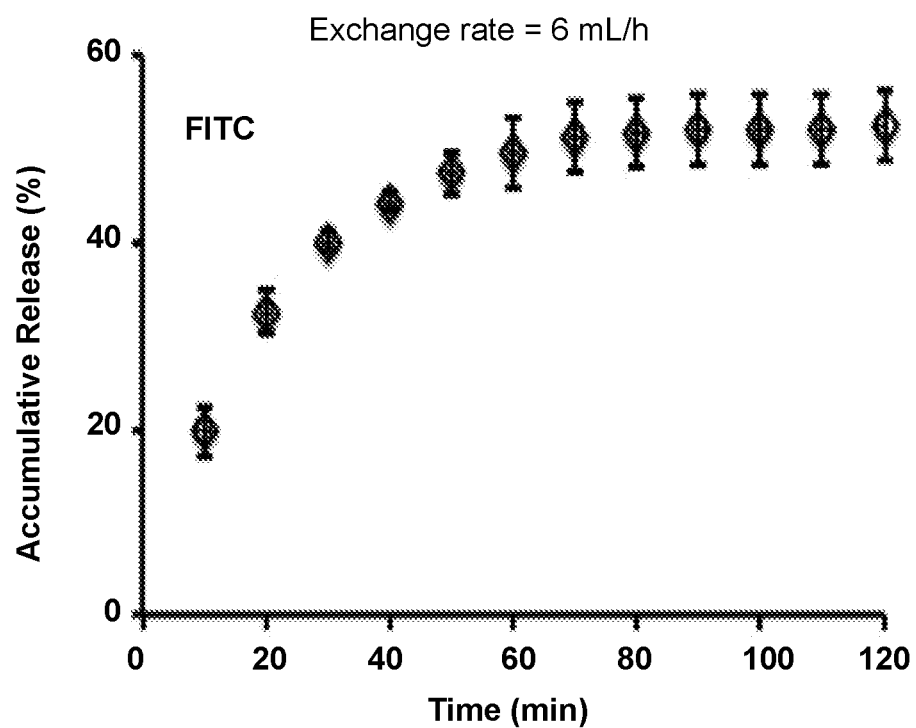

The Release of Adsorbed Molecules from Contact Lenses
Release of FITC-F Compounds from Lenses Contact lenses with attached molecules prepared above were placed into glass vials individually and immersed in 1 mL phosphate buffered saline at room temperature. On day 1, 2, 3, 8, and 15, the phosphate buffered saline solution was removed and the fluorescence of each solution was measured. Then fresh phosphate buffered saline was added to each vial. The amount of FITC-$C_8F_{15}$ (compound 6) or FITC (compound 7) on each lens was calculated as the initial amount on the lens minus the amount released into solution. FIGS. 5A-5D show release of FITC-$C_8F_{15}$ and FITC from Comfilcon A lens at 1 mL/h and 6 mL/h exchange rates. For solution exchange rate of 1 mL/h, the release of unmodified FITC showed a typical burst release profile, and reached plateau with ~60% release within the first 2 h (FIG. 5B). The remaining 40% was likely on the lenses. Burst release is the major hurdle for clinical applications of current contact lens based drug delivery systems. Significantly, the release of FITC-F compound 6 showed a sustained profile with a nearly linear release for the first 6 h (FIG. 5A). The release rate for compound 6 was determined to be 10.5% per hour and reached ~90% at 15 h (FIG. 5A). Upon increasing the solution exchange rate to 6 mL/h, as expected, the release of unmodified FITC quickly reached plateau within 50 min (FIG. 5D). On the other hand, release of FITC-F compound 6 showed a sustained linear release for 120 min (FIG. 5C). The release rate for compound 6 was determined to be 26.5% per hour and reached plateau at 270 min (FIG. 5C). Releasing the drug from contact lenses in such a sustained fashion is beneficial since it greatly improves drug adsorption efficiency and hence efficacy. Another advantage is that it will greatly reduce the amount of drug needed to achieve the same therapeutic efficacy, thus greatly reducing toxicity.

These results showed the release rate increased with faster solution exchange rate, which confirms that the release profiles from contact lens drug delivery model systems are dependent on the experimental setup, and care must be taken to compare results from studies with different setups. The reported tear turnover rate (~100 mL/h) in human subjects varies significantly, and is much lower than the rates used in this experiment. It should be pointed out that the solution in this experiment was changed hourly while tear turnover in the eye is a continuous process, which could result in a different drug release profile. Therefore, it is not feasible to predict the release profile of this system in vivo only based on the solution exchange rates.

Release of F-Cip Compounds from Lenses

Figure 5E:
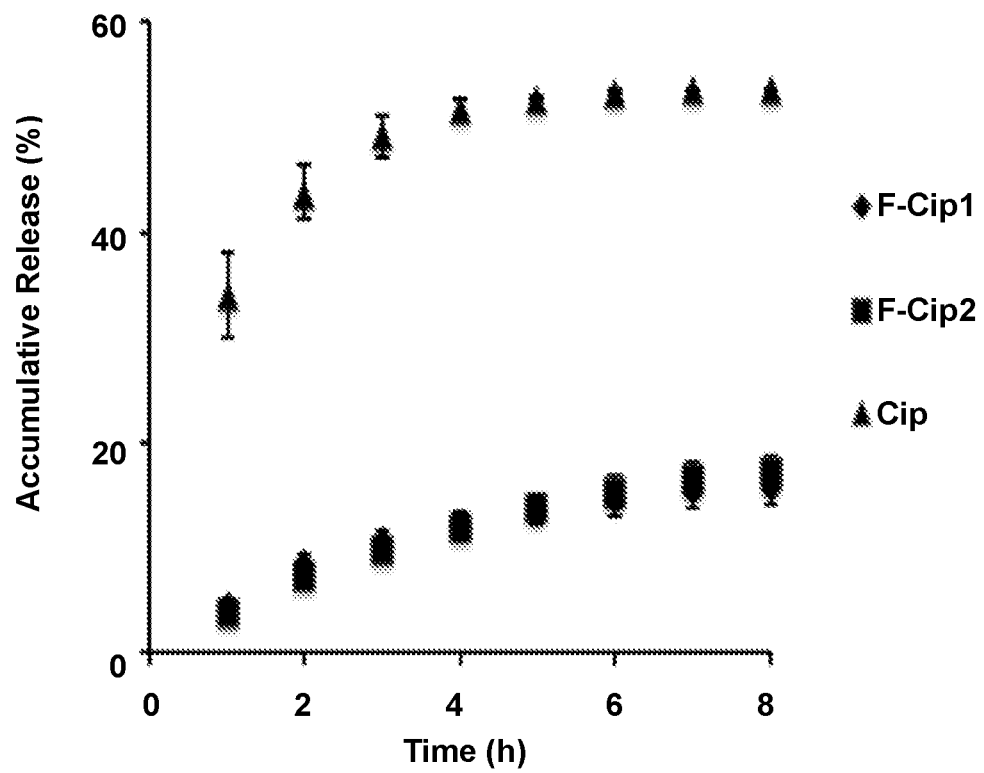
Figure 6:
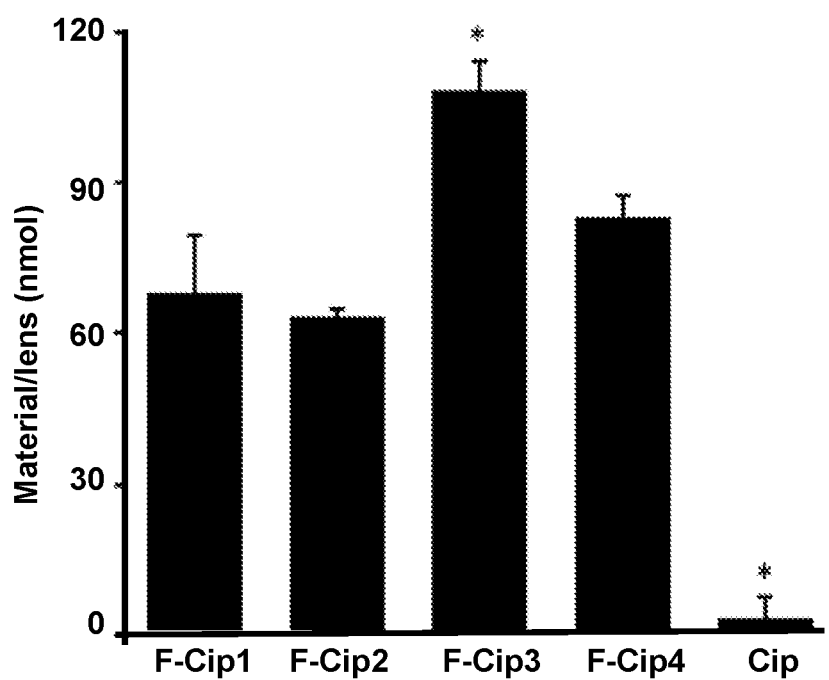
FIG. 6 illustrates the amount of F-Cip compounds 8, 9, 10 and 11, and Cip, (compound 12) loaded onto Comfilcon A lenses. Data are mean±SD from three independent experiments. One-way ANOVA was performed followed by Tukey's test where significance was found. *p<0.05.

FIG. 5E shows the release profile of F-Cip compounds 8 (F-Cip1) and 9 (F-Cip2) and Cip (compound 12) from Comfilcon A lenses over a period of 8 h with a solution exchange rate of 1 mL/h. Compound 12 exhibited a typical burst release profile, that is, most release occurred within the first hour and no more release after 3 h. The plateau was reached at ~60% release, and the remaining 40% were likely on the lenses. Significantly, both F-Cip compounds 8 and 9 exhibited a sustained release profile that is very similar to the release profile of FITC-F compounds shown in FIGS. 5A to 5D. Although the percentage release of F-Cip compounds 8 and 9 within the 8 h period was lower than that of Cip (Compound 12), the amount of F-Cip released was 6 times of that of Cip because the amount of F-Cip loaded onto lenses (~68 nmol/lens) was much more than that of Cip (3.56±4.51 nmol/lens) as shown in FIG. 6. The release profiles of F-Cip compounds 8 and 9 were very similar indicating that only one CF2 group difference in the structures of these two molecules may not affect the overall fluorous interactions between F-Cip and contact lenses, which was also supported by the comparable amounts of F-Cip compounds 8 and 9 loaded onto Comfilcon A lenses. These results indicated that the fluorous attraction is so strong that it holds more molecules for longer time than non-fluorous (Cip) interaction. This is advantageous since greater drug adsorption efficiency results in higher drug efficacy while at the same time greatly reducing the amount of drug needed to achieve the same therapeutic effect, thereby minimizing toxicity.

Example 8

Loading of Modified Ciprofloxacin into Comfilcon A Lenses

As Comfilcon A lenses present the greatest amount of fluorine in the formulation, this type of lens is used for the loading experiment of F-Cip. As shown in FIG. 6, the amount of compounds 8, 9, 10 and 11 loaded onto lens is 67.96±11.50, 68.72±5.28, 108.36±5.95, and 83.31±8.33 nmol/lens, which is about 19, 19, 30 and 23 times more than the amout of Cip loaded (3.56±4.51 nmol/lens) respectively. There are no statistically significant differences for the loading of the compounds 8 and 11 onto the contact lenses but all of them are significantly higher than the amount of Cip.

This result demonstrates that the presence of even a short fluorous tag on the molecule greatly enhances its immobilization onto the fluorocarbon-containing contact lenses. The amount of compound 10 loaded on lenses was significantly more than that for compounds 8, 9 and 11, demonstrating that longer fluorocarbon chain (i.e. stronger interactions between molecules and the lens) facilitated the loading onto lenses. It is also remarkable that after modification, the lenses maintained their transparency.

As shown in FIGS. 4A and 4B, within the range of 200-800 nm, transmission of modified lenses remained ~100% compared to fresh lenses without modification. Therefore, the current simple method has addressed the previously reported issue of loss of transparency of ciprofloxacin-loaded lenses that often exhibited precipitates. The structure difference between compounds 8 and 9 and compound 12 is the fluorinated carbon chain, demonstrating that the presence of fluorine in the molecule greatly facilitated its attachment to fluorine-containing contact lens, which demonstrates that fluorine interactions play an important role in the attachment of fluorinated compounds on fluorine-containing contact lenses. Importantly after modification, the lenses maintained their transparency (~100%) within the visible light range (400-700 nm), compared to fresh lenses without modification.

TABLE 2

IC50 values of fluorinated ciprofloxacin against *Pseudomonas aeruginosa* (PA) ATCC 19660.

| No. | m | n | IC50 (µM) |
|---|---|---|---|
| F-Cip1, Compound 8 | 0 | 2 | 0.63 ± 0.15 |
| F-Cip2, Compound 9 | 0 | 3 | 0.69 ± 0.62 |
| F-Cip3, Compound 10 | 0 | 5 | >40 |
| F-Cip4, Compound 11 | 2 | 1 | >40 |
| Cip, Compound 12 | — | — | 0.13 ± 0.035 |

(n > 3)

Figure 7:
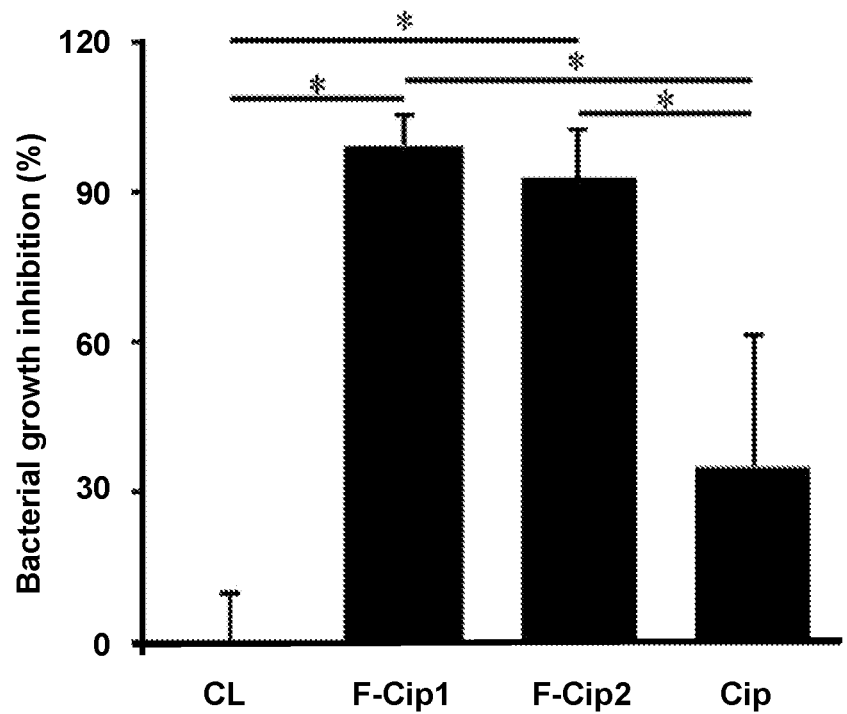
FIG. 7 shows antimicrobial activity against *P. aeruginosa* 19660 in Comfilcon A lenses loaded with compounds 8 and 9 and control compound 12. Data are from three independent experiments expressed as mean±SD. One-way ANOVA is performed followed by Tukey's test where significance is found *p<0.05.

Antimicrobial Activity of Fluorinated Ciprofloxacin Loaded Contact Lenses In Vitro Antimicrobial activity of F-Cip-Loaded Contact Lenses The antimicrobial activity of fluorinated ciprofloxacin 1 (compound 8) and 2 (compound 9) loaded Comfilcon A lenses is tested against *P. aeruginosa* 19660. As shown in FIG. 7, the lenses loaded with compounds 8 and 9 exhibited 99.3% and 93.6% growth inhibition respectively, which is significantly higher than 35.2% by Cip (compound 12) loaded lenses. Table 2 compares the IC50 values against *P. aeruginosa* 19660 for F-Cip compounds with control Cip.

Although compounds 8 and 9 exhibited higher IC50 values (Table 2) against *P. aeruginosa* 19660 compared to ciprofloxacin, the amount of F-Cip1 and F-Cip2 loaded onto Comfilcon A lenses is much more than Cip, which accounts for the need to add statistical analysis to be able to say there is significantly more killing in F-Cip1 and F-Cip2 loaded lenses than Cip loaded lenses. Therefore, the antimicrobial activity of drug-loaded delivery systems does not entirely correlate with the antimicrobial efficacy of the loaded drug, but is also affected by the loaded amount.

It is expected that the antimicrobial activity of this drug delivery system is also dependent on the release profile of drug from vehicles. It is also worth noting that bacteria are also partially cleared from the eye with the continuous tear turnover, which may present a less challenging condition compared to the experimental condition tested here in which bacteria mare maintained in without other clearance mechanisms. Therefore, it is significant that this drug-loaded delivery system exhibited nearly complete killing of bacteria in these demanding conditions, thus proving the antimicrobial efficacy of this drug delivery system of the present invention.

Ex Vivo Infection Model and Antimicrobial Activity of F-Cip Loaded Contact Lenses Due to their similar size and anatomy with human eyes, porcine eyes have been adopted to test the effectiveness of contact lenses in ex vivo models that had a mechanism to mimic the tear turnover. An ex vivo porcine eye infection model was developed, in which culture medium was dripped onto each eye at a rate of four 25 µL drops/min to represent the tear turnover in vivo. Using this system, the antimicrobial activity of compound 8 and compound 12 loaded Comfilcon A lenses against $P.\ aeruginosa$ 19660 was tested. Eyes that are infected with bacteria but not exposed to contact lenses served as control.

Figure 8:
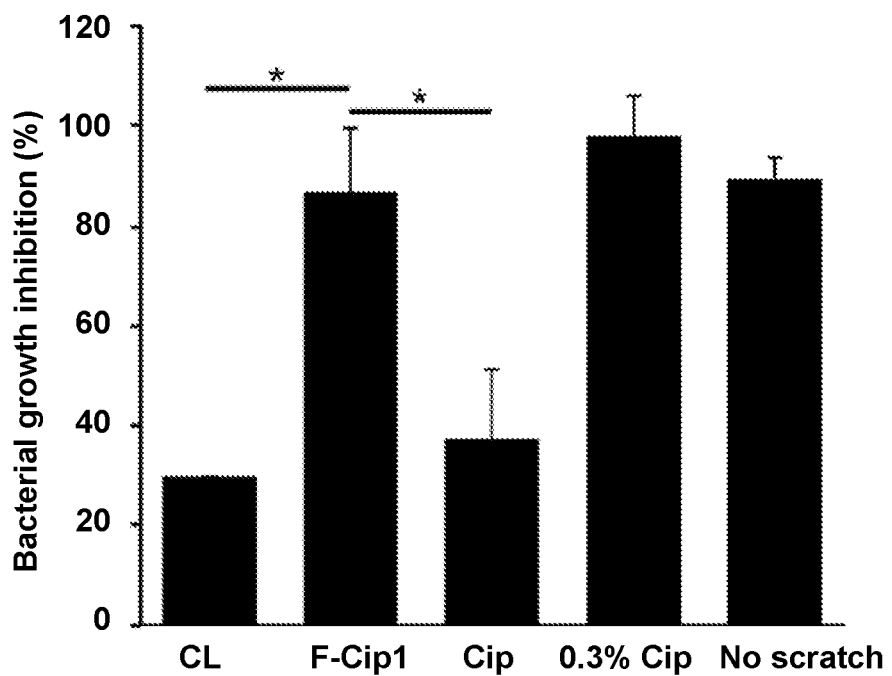
FIG. 8 shows antimicrobial efficacy of modified Comfilcon A lenses in an ex vivo porcine eye infection model. CL: unmodified lenses. 1: lenses modified with F-Cip 1. Cip: lenses modified with Cip. 0.3% Cip: 0.3% ciprofloxacin solution administered in the form of eye drops. No scratch: intact porcine eyes. Statistical analysis is performed using one-way ANOVA followed by Tukey's test comparing to 1 where significance is found. *p<0.05. (n. 3).

As shown in FIG. 8, for eyes with contact lenses modified with compound 8 (F-Cip1), there was significant bacterial growth inhibition (86.8±13.9%) compared to the eyes with unmodified lenses (CL) and compound 12 (Cip) modified lenses, which showed 29.7±12.7% and 37.5±8.2% bacterial growth inhibition, respectively. These results support data from the in vitro antimicrobial assay described above (illustrated in FIG. 7).

Porcine eyes infected with bacteria and treated with 0.3% Cip solution showed 98.1±4.3% bacterial growth inhibition, which is higher than the ones wearing compound 8 modified lenses although this difference is not statistically significant (p=0.70).

In clinical practice, a high concentration (0.3%) of Cip solution is commonly used to treat eye infections and frequent administration is necessary. For example, treatment of relatively mild bacterial conjunctivitis requires one to two drops four times a day, while treatment of sight threatening bacterial ulcers requires drops every 15 min for the first 6 h. It should be noted that the amount of ciprofloxacin in the solution that is used for treatment is more than 100 times the amount of compound 8 (67.96±11.50 nmol/lens, see FIG. 6), yet these two systems showed a comparable efficacy. Therefore, this approach could significantly reduce the amount of drug needed to treat eye infections. For the eyes without scratch wounds, the number of bacteria detected is much less than that of the control eyes indicating that bacteria did not penetrate the intact corneal epithelium and those that grew on top of the ocular surface are most likely washed away during the washing step. Overall, these results showed that contact lenses loaded with F-Cip exhibited antimicrobial activity in an ex vivo model that represents tear clearance in vivo.

Cytotoxicity of Fluorinated Ciprofloxacin Loaded Contact Lenses

Figure 9A:
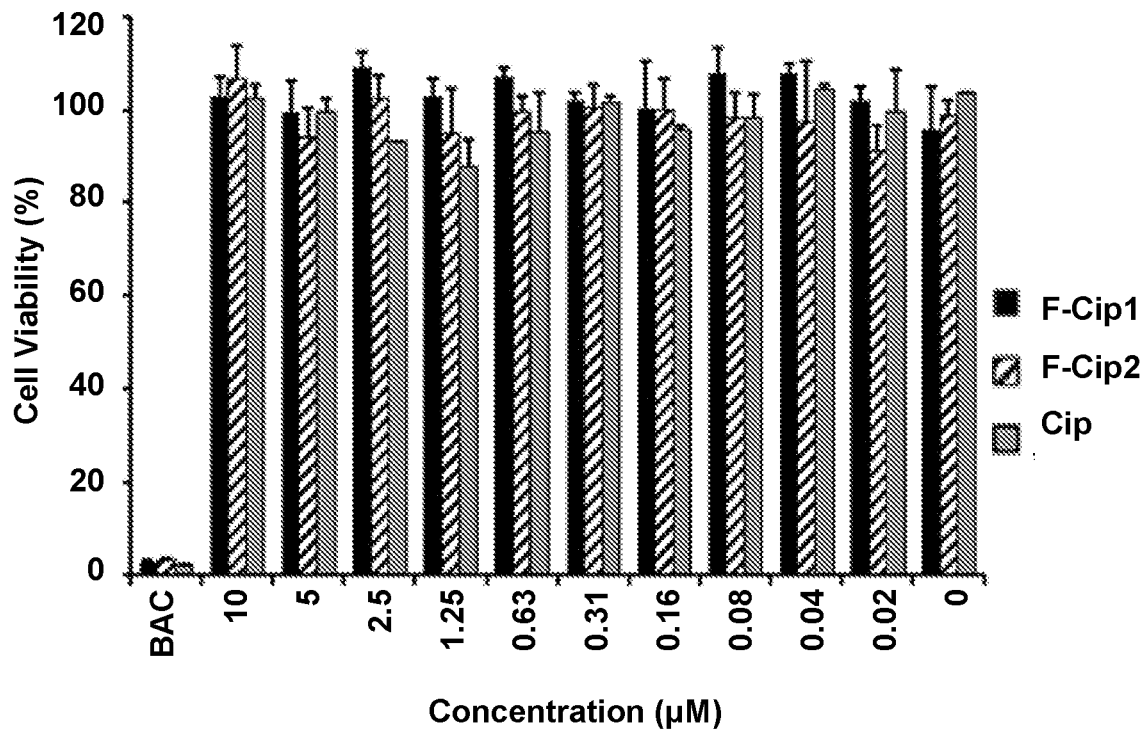
FIGS. 9A-9B illustrate the cytotoxicity of compounds.
Figure 9B:
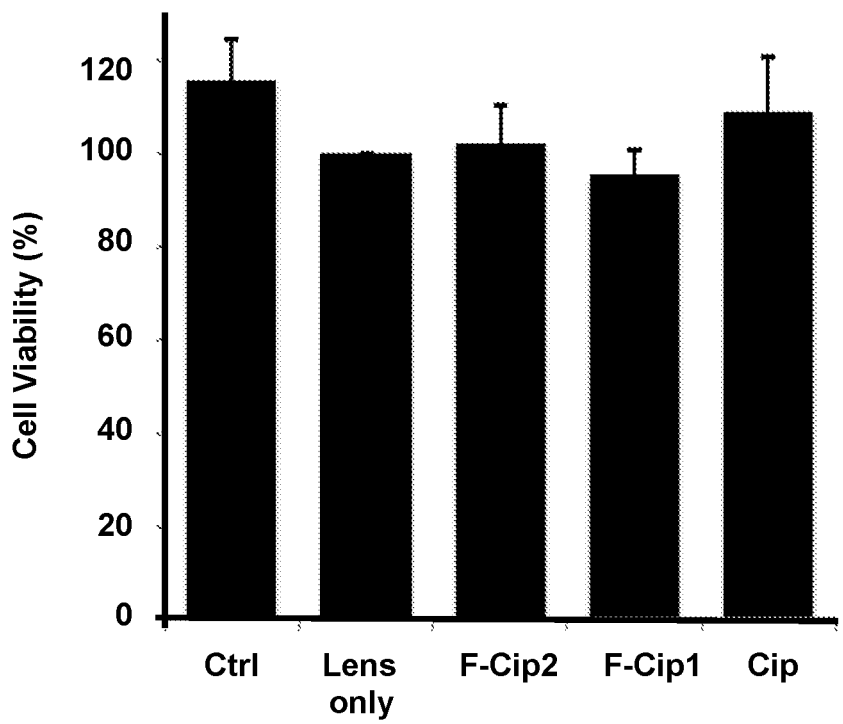

The cytotoxicity of compounds 8 and 9 loaded lenses was tested against a human corneal epithelial cell line. FIG. 9A shows cytotoxicity of compounds 8 and 9 and the unflorinated control compound 12 against human telomerase corneal epithelial cells (hTCEpi) at a series of concentrations between 0 µM and 10 µM. Viability was about 100% with no significant difference among compound 8, compound 9 and compound 12 indicating that modification of Cip with a fluorous tag did not change its cytotoxicity. Benzalkonium chloride (BAC) known to be cytotoxic killed about 100% of cells and served as the positive control. FIG. 9B shows that, cells incubated with untreated lenses exhibited decreased viability compared to cells without any lenses (Ctrl), indicating the potential damaging effect of overnight contact lens wear. For cells incubated with lenses loaded with compounds 8 and 9, and control compound 12, there is no significant difference in toxicity compared to cells incubated with untreated lenses, indicating that loaded drug did not exhibit a toxic effect on this cell line. The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A method for modifying a contact lens to attach drugs to the contact lens, comprising the steps of:

drying the contact lens, wherein the contact lens comprises fluorinated molecules, and wherein the contact lens has at least a 3.7% atomic concentration of fluorinated molecules on surfaces of the contact lens;

incubating the contact lens with at least one fluorinated compound which is the drug for attachment in a medium, wherein the at least one fluorinated compound attaches to the fluorinated molecules in the contact lens through a fluorous interaction to produce a modified contact lens, and wherein the at least one fluorinated compound is a fluorinated ophthalmic drug compound having the chemical structure:

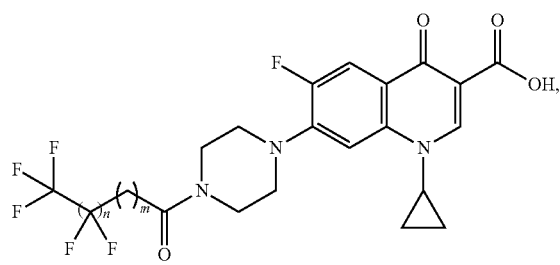

wherein n is 0 or greater and m is 0 or greater; and rinsing the modified contact lens, wherein at least 68 nmol of the at least one fluorinated compound remain attached to the fluorinated molecules in the modified contact lens following rinsing.

2. The method of claim 1, wherein the medium is a buffer or an organic solvent.

3. The method of claim 2, wherein said buffer is phosphate buffered saline.

4. The method of claim 1, wherein the organic solvent is tetrahydrofuran, ethanol or isopropanol.

5. The method of claim 1, wherein the step of incubating the contact lens is performed for about 4 hours to about 24 hours.

6. The method of claim 1, wherein the step of incubating the contact lens is performed at about room temperature.

7. The method of claim 1, wherein said method prevents polymer chain rearrangement of the contact lens.

8. The method of claim 1, wherein said method maintains transparency of the contact lens.

9. The method of claim 1, wherein said contact lens is resistant to microbial agents.

\* \* \* \* \*

UNITED STATES PATENT AND TRADEMARK OFFICE
CERTIFICATE OF CORRECTION

PATENT NO. : 11,529,309 B2
APPLICATION NO. : 16/096603
DATED : December 20, 2022
INVENTOR(S) : Guoting Qin et al.

It is certified that error appears in the above-identified patent and that said Letters Patent is hereby corrected as shown below:

In the Specification

1. In Column 11, Line 65, delete "1 H)," and insert -- 1H), --, therefor.

2. In Column 12, Line 32, delete "79.58" and insert -- -79.59 --, therefor.

3. In Column 12, Line 34, delete "$C_{21}H_8F_8N_3O_4=528.12$;" and insert -- $C_{21}H_{18}F_8N_3O_4=528.12$; --, therefor.

4. In Column 12, Line 56, delete "$CDCl_3$) δ 80.86" and insert -- $CDCl_3$) δ -80.86 --, therefor.

5. In Column 12, Line 57, delete "δ -110.94" and insert -- -110.94 --, therefor.

6. In Column 13, Line 13, delete "80.62" and insert -- -80.62 --, therefor.

7. In Column 14, Line 16, delete "(hv=1486.7 eV)" and insert -- (hv=1486.7 eV) --, therefor.

8. In Column 17, Line 66, delete "$M^{solution}$" and insert -- $M_{solution}$ --, therefor.

In the Claims

9. In Column 22, Line 46, in Claim 1, delete "is" and insert -- is: --, therefor.

10. In Column 23, Line 5, in Claim 4, delete "claim 1," and insert -- claim 2, --, therefor.

Signed and Sealed this
Fourteenth Day of November, 2023

*Katherine Kelly Vidal*
Katherine Kelly Vidal
*Director of the United States Patent and Trademark Office*